United States Patent
Carvalhal et al.

(10) Patent No.: US 9,441,035 B2
(45) Date of Patent: Sep. 13, 2016

(54) CELL CULTURE MEDIA AND METHODS OF ANTIBODY PRODUCTION

(71) Applicant: Genentech, Inc., South San Francisco, CA (US)

(72) Inventors: Veronica Carvalhal, South San Francisco, CA (US); Natarajan Vijayasankaran, South San Francisco, CA (US); Lauren Brown, South San Francisco, CA (US); Thomas DiRocco, South San Francisco, CA (US); Nathan McKnight, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 40 days.

(21) Appl. No.: 14/211,467

(22) Filed: Mar. 14, 2014

(65) Prior Publication Data

US 2014/0308273 A1    Oct. 16, 2014

Related U.S. Application Data

(60) Provisional application No. 61/801,247, filed on Mar. 15, 2013.

(51) Int. Cl.
| | | |
|---|---|---|
| *C07K 16/22* | (2006.01) | |
| *C12N 5/00* | (2006.01) | |
| *C12N 5/10* | (2006.01) | |
| *A61K 39/395* | (2006.01) | |
| *C07K 16/00* | (2006.01) | |

(52) U.S. Cl.
CPC .............. *C07K 16/22* (2013.01); *C07K 16/00* (2013.01); *C07K 2317/14* (2013.01); *C07K 2317/24* (2013.01); *C07K 2317/76* (2013.01); *C12N 2510/02* (2013.01)

(58) Field of Classification Search
CPC .. C07K 16/22; C07K 16/00; C07K 2317/14; C07K 2317/76; C07K 2317/24; C12N 2510/02; C12N 2800/107; C12N 2800/10; C12N 2500/00; C12N 2500/76; C12N 2500/80; C12N 2500/10; C12N 2500/25; C12N 2511/00; C12N 5/068
See application file for complete search history.

(56) References Cited

U.S. PATENT DOCUMENTS

| | | |
|---|---|---|
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,122,469 A * | 6/1992 | Mather ............... C12N 5/0037 435/383 |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,248,516 B1 | 6/2001 | Winter et al. |
| 6,417,429 B1 | 7/2002 | Hein et al. |
| 6,420,548 B1 | 7/2002 | Vézina et al. |
| 6,528,286 B1 * | 3/2003 | Ryll ................... C12N 5/0043 435/200 |
| 6,884,879 B1 * | 4/2005 | Baca ................... C07K 16/22 435/320.1 |
| 6,919,436 B2 | 7/2005 | Lihme et al. |
| 6,982,321 B2 | 1/2006 | Winter |
| 7,060,269 B1 | 6/2006 | Baca et al. |
| 7,078,492 B2 | 7/2006 | Pirofski et al. |
| 7,087,409 B2 | 8/2006 | Barbas et al. |
| 7,125,978 B1 | 10/2006 | Vézina et al. |
| 7,169,901 B2 | 1/2007 | Baca et al. |
| 7,189,826 B2 | 3/2007 | Rodman |
| 7,227,004 B2 | 6/2007 | Kim |
| 7,297,334 B2 | 11/2007 | Baca et al. |
| 7,807,142 B2 | 10/2010 | Chen et al. |
| 8,956,830 B2 * | 2/2015 | Prentice ............... C12P 21/005 435/325 |
| 2005/0026229 A1 | 2/2005 | Reiter et al. |

(Continued)

FOREIGN PATENT DOCUMENTS

| | | |
|---|---|---|
| EP | 0073657 B1 | 12/1990 |
| EP | 0402226 A1 | 12/1990 |

(Continued)

OTHER PUBLICATIONS

Li et al., mAbs 2(5): 466-477, Sep./Oct. 2010.*

(Continued)

*Primary Examiner* — Phuong Huynh

(74) *Attorney, Agent, or Firm* — Morrison & Foerster LLP

(57) ABSTRACT

Cell culture media are provided herein as are methods of using the media for cell culture and antibody production from cells. Compositions comprising antibodies and fragments thereof, produced by the methods herein are also provided.

84 Claims, No Drawings

(56) References Cited

U.S. PATENT DOCUMENTS

| | | | |
|---|---|---|---|
| 2005/0100546 A1 | 5/2005 | Jakobovits et al. | |
| 2005/0176122 A1 | 8/2005 | Lihme et al. | |
| 2005/0276823 A1 | 12/2005 | Cini et al. | |
| 2005/0287149 A1 | 12/2005 | Keler et al. | |
| 2006/0059575 A1 | 3/2006 | Kusunoki et al. | |
| 2006/0115901 A1* | 6/2006 | Valamehr | C12N 5/0037 435/404 |
| 2006/0183887 A1 | 8/2006 | Jakobovits et al. | |
| 2006/0258841 A1 | 11/2006 | Michl et al. | |
| 2008/0254514 A1* | 10/2008 | Knudsen | C12N 9/6437 435/71.1 |
| 2010/0068210 A1 | 3/2010 | Ji et al. | |
| 2010/0098725 A1 | 4/2010 | Liu et al. | |
| 2011/0091936 A1* | 4/2011 | Gawlitzek | C12N 5/0018 435/69.3 |
| 2011/0129926 A1 | 6/2011 | Fike et al. | |
| 2011/0207174 A1* | 8/2011 | Katayama | C07K 5/081 435/69.6 |
| 2012/0177640 A1 | 7/2012 | Burg et al. | |
| 2013/0157356 A1* | 6/2013 | Barnett | C07K 14/765 435/346 |

FOREIGN PATENT DOCUMENTS

| | | |
|---|---|---|
| EP | 0183070 B1 | 10/1991 |
| EP | 0404097 B1 | 9/1996 |
| EP | 0244234 B2 | 11/2001 |
| WO | 87/00195 A1 | 1/1987 |
| WO | 90/03430 A1 | 4/1990 |
| WO | 90/13646 A1 | 11/1990 |
| WO | 91/00360 A1 | 1/1991 |
| WO | 91/10741 A1 | 7/1991 |
| WO | 92/09690 A2 | 6/1992 |
| WO | 93/01161 A1 | 1/1993 |
| WO | 93/06213 A1 | 4/1993 |
| WO | 93/08829 A1 | 5/1993 |
| WO | 93/16185 A2 | 8/1993 |
| WO | 94/04690 A1 | 3/1994 |
| WO | 94/11026 A2 | 5/1994 |
| WO | 96/07754 A1 | 3/1996 |
| WO | 96/27011 A1 | 9/1996 |
| WO | 96/33735 A1 | 10/1996 |
| WO | 96/34096 A1 | 10/1996 |
| WO | 98/24893 A2 | 6/1998 |
| WO | 03/046162 A2 | 6/2003 |
| WO | 2012/145682 A1 | 10/2012 |

OTHER PUBLICATIONS

Kaschak et al., mAbs 3(6): 577-583, 2011.*
Kim et al., Appl Microbiol Biotechnol 83: 639-648, 2009.*
Heidemann et al., Cytotechnology 32: 157-167, 2000.*
Yazaki et al., "Expression of Recombinant Antibodies in Mammalian Cell Lines", Methods in Molecular Biology, vol. 248, 2004, pp. 255-268.
Zapata et al., "Engineering Linear F(ab')2 Fragments for Efficient Production in *Escherichia coli* and Enhanced Antiproliferative Activity", Protein Engineering, vol. 8, No. 10, 1995, pp. 1057-1062.
Zhu et al., "Probing the Antibody-Catalyzed Water-Oxidation Pathway at Atomic Resolution", PNAS, vol. 101, No. 8, Feb. 24, 2004, pp. 2247-2252.
Babu et al., "Tryptophan as an Endogenous Photosensitizer to Elicit Harmful Effects of Ultraviolet B", Indian Journal of Biochemistry and Biophysics, vol. 29, Jun. 1992, pp. 296-298.
Baltazar et al., "Antioxidant Properties and Associated Mechanisms of Salicylates", Current Medicinal Chemistry, vol. 18, Issue 21, 2011, pp. 3252-3264.
Barbas III et al., "Semisynthetic Combinatorial Antibody Libraries: A Chemical Solution to the Diversity Problem", PNAS, Proceedings of the National Academy of Sciences, vol. 89, May 1992, pp. 4457-4461.
Barbas III et al., "Assembly of Combinatorial Antibody Libraries on Phage Surfaces: The Gene III Site", Proceedings of the National Academy of Sciences, vol. 88, Sep. 1991, pp. 7978-7982.
Barnes et al., "Methods for Growth of Cultured Cells in Serum-Free Medium", Analytical Biochemistry, vol. 102, 1980, pp. 255-270.
Bass et al., "Hormone Phage: An Enrichment Method for Variant Proteins With Altered Binding Properties", Proteins: Structure, Function, and Genetics, vol. 8, 1990, pp. 309-314.
Bent et al., "Excited State Chemistry of Aromatic Amino Acids and Related Peptides. III, Tryptophan", Journal of the American Chemical Society, vol. 97, No. 10, May 14, 1975, pp. 2612-2619.
Bertolotti-Ciarleta et al., "Impact of Methionine Oxidation on the Binding of Human IgG1 to FcRn and Fcγ Receptors", Molecular Immunology, vol. 46, May 2009, pp. 1878-1882.
Boerner et al., "Production of Antigen-specific Human Monoclonal Antibodies from in Vitro-primed Human Splenocytes", The Journal of Immunology, vol. 147, No. 1, Jul. 1, 1991, pp. 86-95.
Brennan et al., "Preparation of Bispecific Antibodies by Chemical Recombination of Monoclonal Immunoglobulin G1 Fragments", Science, vol. 229, Jul. 5, 1985, pp. 81-83.
Brodeur et al., "Mouse-Human Myeloma Partners for the Production of Heterohybridomas", Monoclonal Antibody Production Techniques and Applications, Chapter 4, 1987, pp. 51-63.
Bruggemann et al., "Designer Mice: The Production of Human Antibody Repertoires in Transgenic Animals", Year Immunology, vol. 7, 1993, pp. 33-40.
Capelle et al., "High Throughput Screening of Protein Formulation Stability: Practical Considerations", European Journal of Pharmaceutics and Biopharmaceutics, vol. 65, 2007, pp. 131-148.
Carter et al., "High Level *Escherichia coli* Expression and Production of a Bivalent Humanized Antibody Fragment", Biotechnology, vol. 10, Feb. 1992, pp. 163-167.
Carter et al., "Humanization of an Anti-p185HER2 Antibody for Human Cancer Therapy", Proc. Natl. Acad. Sci., vol. 89, May 1992, pp. 4285-4289.
Champe et al., "Monoclonal Antibodies That Block the Activity of Leukocyte Function-associated Antigen 1 Recognize Three Discrete Epitopes in the Inserted Domain of CDLLa", The Journal of Biological Chemistry, vol. 270, No. 3, 1995, pp. 1388-1394.
Chao et al., "Modification of Protein Surface Hydrophobicity and Methionine Oxidation by Oxidative Systems", PNAS, Proceedings of the National Academy of Sciences, vol. 94, Apr. 1997, pp. 2969-2974.
Charlton, Keith A., "Expression and Isolation of Recombinant Antibody Fragments in *E. coli*", Methods in Molecular Biology, vol. 248, 2003, pp. 245-254.
Chothia et al., "Canonical Structures for the Hypervariable Regions of Immunoglobulins", Journal of Molecular Biology, vol. 196, 1987, pp. 901-917.
Christen et al., "Antioxidant Activities of Some Tryptophan Metabolites: Possible Implication for Inflammatory Diseases", Proceedings of the National Academy of Sciences, vol. 87, Apr. 1990, pp. 2506-2510.
Clackson et al., "Making Antibody Fragments Using Phage Display Libraries", Nature, vol. 352, Aug. 15, 1991, pp. 624-628.
Cole et al., "The EBV-Hybridoma Technique and its Application to Human Lung Cancer", Monoclonal Antibodies and Cancer Therapy, 1985, pp. 77-96.
Creed, David, "The Photophysics and Photochemistry of the Near-UV Absorbing Amino Acids-I. Tryptophan and Its Simple Derivatives", Photochemistry and Photobiology, vol. 39, No. 4, 1984, pp. 537-562.
Davies, Michael J., "Singlet Oxygen-Mediated Damage to Proteins and its Consequences", Biochemical and Biophysical Research Communications, vol. 305, 2003, pp. 761-770.
Duchosal et al., "Immunization of hu-PBL—SCID Mice and the Rescue of Human Monoclonal Fab Fragments Through Combinatorial Libraries", Nature, vol. 355, Jan. 16, 1992, pp. 258-262.
Embleton et al., "In-Cell PCR From mRNA: Amplifying and Linking the Rearranged Immunoglobulin Heavy and Light Chain V-genes within Single Cells", Nucleic Acids Research, vol. 20, Issue 15, 1992, pp. 3831-3837.
Even et al., "Serum-free Hybridoma Culture: Ethical, Scientific and Safety Considerations", Trends in Biotechnology, vol. 24, Issue 3, Mar. 2006, pp. 105-108.

(56) References Cited

OTHER PUBLICATIONS

Fellouse et al., "Synthetic Antibodies from a Four-amino-acid Code: A Dominant Role for Tyrosine in Antigen Recognition", PNAS, vol. 101, No. 34, 2004, pp. 12467-12472.
Fishwild et al., "High-Avidity Human IgGK Monoclonal Antibodies Frotn a Novel Strain of Minilocus Transgenic Mice", Nature Biotechnology, vol. 14, Jul. 1996, pp. 845-851.
Fleer et al., "Stable Multicopy Vectors for High-Level Secretion of Recombinant Human Serum Albumin by Kluyveromyces Yeasts", Biotechnology, vol. 9, Oct. 1991, pp. 968-975.
Franek, Frantisek, "Oligopeptides as Tools for Improving Productivity of Hybridoma Cells Cultures", Trends in Monoclonal Antibody Research, Chapter VI, 2005, pp. 111-122.
Frokjaer et al., "Protein Drug Stability: A Formulation Challenge", Nature Reviews Drug Discovery, vol. 4, Apr. 2005, pp. 298-306.
Gerngross, Tillman U., "Advances in the Production of Human Therapeutic Proteins in Yeasts and Filamentous Fungi", Nature Biotechnology, vol. 22, No. 11, Nov. 2004, pp. 1409-1414.
Goding, James W., "Production of Monoclonal Antibodies", Monoclonal Antibodies: Principles and Practice, Chapter 3 and Chapter 4, 1983, pp. 56-97.
Graham et al., "Characteristics of a Human Cell Line Transformed by DNA from Human Adenovirus Type 5", Journal of General Virology, vol. 36, 1977, pp. 59-72.
Gram et al., "In Vitro Selection and Affinity Maturation of Antibodies from a Naive Combinatorial Immunoglobulin Library", PNAS, vol. 89, Apr. 1992, pp. 3576-3580.
Griffiths et al., "Human Anti-self Antibodies with High Specificity from Phage Display Libraries", The EMBO Journal vol. 12, No. 2, 1993, pp. 725-734.
Gruber et al., "Efficient Tumor Cell Lysis Mediated by a Bispecific Single Chain Antibody Expressed in *Escherichia coli*", The Journal of Immunology, vol. 152, No. 11, 1994, pp. 5368-5374.
Guss et al., "Structure of the IgG-binding Regions of *Streptococcal* Protein G", The EMBO Journal, vol. 5, No. 7, 1986, pp. 1567-1575.
Ham et al., "Media and Growth Requirements", Methods in Enzymology, vol. 58, 1979, pp. 44-93.
Hamers-Casterman et al., "Naturally Occurring Antibodies Devoid of Light Chains.", Nature, vol. 363, Jun. 3, 1993, pp. 446-448.
Hammerling et al., "Monoclonal Antibodies and T-Cell Hybridomas", Research Monographs in Immunology, vol. 3, 1981, 14 pages.
Harris, W. J., "Production of Humanized Monoclonal Antibodies for in Vivo Imaging and Therapy", Therapeutic Monoclonals, vol. 23, 1995, pp. 1035-1038.
Hawkins et al., "Selection of Phage Antibodies by Binding Affinity: Mimicking Affinity Maturation", Journal of Molecular Biology, vol. 226, 1992, pp. 889-896.
Hogrefe et al., "A Bacteriophage Lambda Vector for the Cloning and Expression of Immunoglobulin Fab Fragments on the Surface of Filamentous Phage", Gene, vol. 128, 1993, pp. 119-126.
Holliger et al., "Diabodies": Small Bivalent and Bispecific Antibody Fragments, Proceedings of the National Academy of Sciences, USA, vol. 90, Jul. 1993, pp. 6444-6448.
Hongo et al., "Development and Characterization of Murine Monoclonal Antibodies to the Latency-Associated Peptide of Transforming Growth Factor β1", Hybridoma. vol. 14, No. 3, 1995, pp. 253-260.
Pluckthun Andreas, "Mono- and Bivalent Antibody Fragments Produced in *Escherichia coli*: Engineering, Folding and Antigen Binding", Immunological Reviews, No. 130, 1992, pp. 151-188.
Presta, Leonard G., "Antibody Engineering", Current Opinion in Structural Biology, vol. 2, 1992, pp. 593-596.
Presta et al., "Humanization of an Antibody Directed Against IgE", The Journal of Immunology, vol. 151, No. 5, Sep. 1, 1993, pp. 2623-2632.
Presta et al., "Humanization of an Anti-Vascular Endothelial Growth Factor Monoclonal Antibody for the Therapy of Solid Tumors and other Disorders", Cancer Research, vol. 57, 1997, pp. 4593-4599.
Prousek Josef, "Fenton Chemistry in Biology and Medicine", Pure and Applied Chemistry, vol. 79, No. 12, 2007, pp. 2325-2338.
Reyes et al., "Expression of Human β-Interferon cDNA Under the Control of a Thymidine Kinase Promoter from Herpes Simplex Virus", Nature, vol. 297, Jun. 17, 1982, pp. 598-601.
Riechmann et al., "Reshaping Human Antibodies for Therapy", Nature, vol. 332, Mar. 24, 1988, pp. 323-327.
Pluckthun A., "Antibodies from *Escherichia coli*", Chapter II, The Pharmacology of Monoclonal Antibodies, 1994, pp. 269-315.
Sastry et al., "Cloning of the Immunological Repertoire in *Escherichia coli* for Generation of Monoclonal Catalytic Antibodies: Construction of a Heavy Chain Variable Region-specific cDNA Library", Proceedings of the National Academy of Sciences, vol. 86, Aug. 1989, pp. 5728-5732.
Shalaby et al., "Development of Humanized Bispecitic Antibodies Reactive with Cytotoxic Lymphocytes and Tumor Cells Overexpressing the HER2 Protooncogene", The Journal of Experimental Medicine, vol. 175, Jan. 1992, pp. 217-225.
Sheriff et al., "Redefining the Minimal Antigen-binding Fragment", Nature Structural and Molecular Biology, vol. 3, No. 9, Sep. 1996, pp. 733-736.
Sidhu et al., "Phage-Displayed Antibody Libraries of Synthetic Heavy Chain Complementarity Determining Regions", Journal of Molecular Biology, vol. 338, 2004, pp. 299-310.
Sims et al., "A Humanized CD18 Antibody Can Block Function Without Cell Destruction", The Journal of Immunology, vol. 151, No. 4, Aug. 15, 1993, pp. 2296-2308.
Skerra, Arne, "Bacterial Expression of Immunoglobulin Fragments", Current Opinion in Immunology, vol. 5, 1993, pp. 256-262.
Sreedhara, "Role of Surface Exposed Tryptophan as Substrate Generators for the Antibody Catalyzed Water Oxidation Pathway", Molecular Pharmaceutics, vol. 10, 2013, pp. 278-288.
Stinchcomb et al., "Isolation and Characterisation of a Yeast Chromosomal Replicator", Nature, vol. 282, Nov. 1, 1979, pp. 39-43.
Suresh et al., "Bispecific Monoclonal Antibodies from Hybrid Hybridomas", Methods in Enzymology, vol. 121, 1986, pp. 210-228.
Tomlinson et al., "The Repertoire of Human Germline VH Sequences Reveals About Fifty Groups of VH Segments with Different Hypervariable Loops", Journal of Molecular Biology, vol. 227, 1992, pp. 776-798.
Traunecker et al., "Bispecific Single Chain Molecules (Janusins) Target Cytotoxic Lymphocytes on HIV Infected Cells", The EMBO Journal, vol. 10, No. 12, 1991, pp. 3655-3659.
Tutt et al., "Trispecific F(ab')3 Derivatives that use Cooperative Signaling via the TCRCD3 Complex and CD2 to Activate and Redirect Resting Cytotoxic T cells", Journal of Immunology, vol. 147, No. 1, Jul. 1, 1991, pp. 60-69.
Urlaub et al., "Isolation of Chinese Hamster Cell Mutants Deficient in Dihydrofolate Reductase Activity", Proc. Natl. Acad. Sci., vol. 77, No. 7, Jul. 1980, pp. 4216-4220.
Van Den Berg et al., "Kluyveromyces as a Host for Heterologous Gene Expression: Expression and Secretion of Prochymosin", Biotechnology, vol. 8, Feb. 1990, pp. 135-139.
Van Dijk et al., "Human Antibodies as Next Generation Therapeutics", Current Opinion in Chemical Biology, vol. 5, 2001, pp. 368-374.
Vaswani et al., "Humanized Antibodies as Potential Therapeutic Drugs", Annals of Allergy, Asthma and Immunology, vol. 81, Aug. 1998, pp. 105-115.
Verhoeyen et al., "Reshaping Human Antibodies: Grafting an Antilysozyme Activity", Science, vol. 239, 1988, pp. 1534-1536.
Vollmers et al., "Death by Stress: Natural IgM-Induced Apoptosis", Methods and Findings in Experimental and Clinical Pharmacology, vol. 27, No. 3, 2005, pp. 185-191.
Vollmers et al., "The "Early Birds": Natural IgM Antibodies and Immune Surveillance", Histology and Histopathology, vol. 20, 2005, pp. 927-937.
Wang et al., "Impact of Methionine Oxidation in Human IgG1 Fc on Serum Half-Life of Monoclonal Antibodies", Molecular Immunology, vol. 48, 2011, pp. 860-866.

(56) References Cited

OTHER PUBLICATIONS

Ward et al., "Binding Activities of a Repertoire of Single Immunoglobulin Variable Domains Secreted from *Escherichia coli*", Nature, vol. 341, Oct. 12, 1989, pp. 544-546.
Waterhouse et al., "Combinatorial Infection and In Vivo Recombination: A Strategy for Making Large Phage Antibody Repertoires", Nucleic Acids Research, 1993, vol. 21, No. 9, 1993, pp. 2265-2266.
Wei et al., "Identification of a Single Tryptophan Residue as Critical for Binding Activity in a Humanized Monoclonal Antibody against Respiratory Syncytial Virus", Analytical Chemistry, vol. 79, No. 7, Apr. 1, 2007, pp. 2797-2805.
Wentworth et al., "Antibodies have the Intrinsic Capacity to Destroy Antigens", PNAS, vol. 97, No. 20, Sep. 26, 2000, pp. 10930-10935.
Wentworth et al., "Antibody Catalysis of the Oxidation of Water", Science, vol. 293, Sep. 7, 2001, pp. 1806-1811.
Werber et al., "Analysis of 2,2-Azobis (2-Amidinopropane) Dihydrochloride Degradation and Hydrolysis in Aqueous Solutions", Journal of Pharmaceutical Sciences, vol. 100, No. 8, Aug. 2011, pp. 3307-3315.
Williams et al., "Cloning and Sequencing of Human Immunoglobulin VA Gene Segments", European Journal of Immunology, vol. 23, 1993, pp. 1456-1461.
Winter et al., "Making Antibodies by Phage Display Technology", Annual Review of Immunology, vol. 12, 1994, pp. 433-455.
Xu et al., "Diversity in the CDR3 Region of VH Is Sufficient for Most Antibody Specificities", Immunity, vol. 13, Jul. 2000, pp. 37-45.
Yaniv, Moshe, "Enhancing Elements for Activation of Eukaryotic Promoters", Nature, vol. 297, May 6, 1982, pp. 17-18.
Hoogenboom et al., "By-passing Immunisation: Human Antibodies from Synthetic Repertoires of Germline VH Gene Segments Rearranged In Vitro", Journal of Molecular Biology, vol. 227, 1992, pp. 381-388.
Hoogenboom, Hennie R., "Overview of Antibody Phage-Display Technology and Its Applications", Methods in Molecular Biology, vol. 178, 2001, pp. 1-37.
Hoogenboom' et al., "Multi-Subunit Proteins on the Surface of Filamentous Phage: Methodologies for Displaying Antibody (Fab) Heavy and Light Chains", Nucleic Acids Research, vol. 19, No. 15, 1991, pp. 4133-4137.
Hudson et al., "Engineered Antibodies", Nature Medicine, vol. 9, No. 1, Jan. 2003, pp. 129-134.
Hurle et al., "Protein Engineering Techniques for Antibody Humanization", Current Opinion in Biotechnology, vol. 5, Aug. 1994, pp. 428-433.
Igarashi et al., "Photoreactivity of Amino Acids: Tryptophan-induced Photochemical Events via Reactive Oxygen Species Generation", Analytical Sciences, vol. 23, 2007, pp. 943-948.
Jakobovits et al., "Analysis of Homozygous Mutant Chimeric Mice: Deletion of the Immunoglobulin Heavy-chain Joining Region Blocks B-cell Development and Antibody Production", Proceedings of the National Academy of Sciences, vol. 90, Mar. 1993, pp. 2551-2555.
Jakobovits et al., "Germ-line Transmission and Expression of a Human-derived Yeast Artificial Chromosome", Nature, vol. 362, Mar. 18, 1993, pp. 255-258.
Ji et al., "Methionine, Tryptophan, and Histidine Oxidation in a Model Protein, PTH: Mechanisms and stabilization", Journal of Pharmaceutical Sciences, vol. 98, No. 12, Dec. 2009, pp. 4485-4500.
Johnson et al., "The Kabat Database and a Bioinformatics Example", Methods in Molecular Biology, Antibody Engineering: Methods Protocols, vol. 248, 2004, pp. 11-25.
Jones, Andrew, "Analysis of Polypeptides and Proteins", Advanced Drug Delivery Reviews, vol. 10, 1993, pp. 29-90.
Jones et al., "Materials and Methods: Rapid PCR-Cloning of Full-Length Mouse Immunoglobulin Variable Regions", Biotechnology, vol. 9, Jan. 1991, pp. 88-89.
Jones, Elizabeth W., "Proteinase Mutants of *Saccharomyces cerevisiae*", Genetics, vol. 85, Jan. 1977, pp. 23-33.
Jones et al., "Replacing the Complementarity-Determining Regions in a Human Antibody with Those from a Mouse", Nature, vol. 321, May 29, 1986, pp. 522-525.
Kelley, Brian, "Industrialization of mAb Production Technology", mAbs, vol. 1, No. 5, 2009, pp. 443-452.
Kohler et al., "Continuous Cultures of Fused Cells Secreting Antibody of Predefined Specificity", Nature vol. 256, Aug. 7, 1975, pp. 495-497.
Kostelny et al., "Formation of a Bispecific Antibody by the Use of Leucine Zippers", The Journal of Immunology, vol. 148, No. 5, Mar. 1, 1992, pp. 1547-1553.
Kozbor et al., "A Human Hybrid Myeloma for Production of Human Monoclonal Antibodies", The Journal of Immunology, vol. 133, No. 6, Dec. 1984, pp. 3001-3005.
Lam et al., "Antioxidants for Prevention of Methionine Oxidation in RecombinantMonoclonal Antibody HER2", Journal of Pharmaceutical Sciences, vol. 86, No. 11, Nov. 1997, pp. 1250-1255.
Lam et al., "Site-Specific Tryptophan Oxidation Induced by Autocatalytic Reaction of Polysorbate 20 in Protein Formulation", Pharmaceutical Research, vol. 28, 2011, pp. 2543-2555.
Lee et al., "Bivalent Antibody Phage Display Mimics Natural Immunoglobulin", Journal of Immunological Methods, vol. 284, 2004, pp. 119-132.
Lee et al., "High-Affinity Human Antibodies from Phage-displayed Synthetic Fab Libraries with a Single Framework Scaffold", Journal of Molecular Biology, vol. 340, 2004, pp. 1073-1093.
Leung et al., "A Method for Random Mutagenesis of a Defined DNA Segment using a Modified Polymerase Chain Reaction", Technique—A Journal of Methods in Cell and Molecular Biology, vol. 1, No. 1, Aug. 1989, pp. 11-15.
Levine et al., "Methionine Residues as Endogenous Antioxidants in Proteins", Proceedings of the National Academy of Sciences of the United States of America, vol. 93, Dec. 1996, pp. 15036-15040.
Li et al., "Cell Culture Processes for Monoclonal Antibody Production", mAbs, vol. 2, No. 5, 2010, pp. 466-477.
Li et al., "Chemical Instability of Protein Pharmaceuticals : Mechanisms of Oxidation and Strategies for Stabilization", Biotechnology and Bioengineering, vol. 48, 1995, pp. 490-500.
Li et al., "Human Antibodies for Immunotherapy Development Generated via a Human B Cell Hybridoma Technology", PNAS, vol. 103, No. 10, Mar. 7, 2006, pp. 3557-3562.
Li et al., "Optimization of Humanized IgGs in Glycoengineered Pichia Pastoris", Nature Biotechnology, vol. 24, No. 2, Feb. 2006, pp. 210-215.
Li et al., "Small dsRNAs Induce Transcriptional Activation in Human Cells", PNAS, vol. 103, No. 46, Nov. 2006, pp. 17337-17342.
Lindmark et al., "Binding of Immunoglobulins to Protein A and Immunoglobulin Levels in Mammalian Sera", Journal of Immunological Methods, vol. 62, 1983, pp. 1-13.
Lonberg et al., "Antigen-Specific Human Antibodies from Mice Comprising Four Distinct Genetic Modifications", Nature, vol. 368, Apr. 28, 1994, pp. 856-859.
Lonberg et al., "Human Antibodies from Transgenic Mice", International Reviews of Immunology, vol. 13, 1995, pp. 65-93.
Manning et al., "Stability of Protein Pharmaceuticals: An Update", Pharmaceutical Research, vol. 27, No. 4, Apr. 2010, pp. 544-575.
Marks et al., "By-Passing Immunization: Building High Affinity Human Antibodies by Chain Shuffling", Biotechnology, vol. 10, Jul. 1992, pp. 779-783.
Marks et al., "By-Passing Immunization: Human Antibodies from V-gene Libraries Displayed on Phage", Journal of Molecular Biology, vol. 222, 1991, pp. 581-597.
Mather et al., "Culture of Testicular Cells in Hormone-Supplemented Serum-Free Medium", Annals of the New York Academy of Sciences, Testicular Cell Culture, 1982, pp. 44-68.
Mather, Jennie P., "Establishment and Characterization of Two Distinct Mouse Testicular Epithelial Cell Lines", Biology of Reproduction, vol. 23, 1980, pp. 243-252.
Matsuda et al., "Structure and Physical Map of 64 Variable Segments in the 3' 0.8—Megabase Region of the Human Immunoglobulin Heavy-Chain Locus", Nature Genetics, vol. 3, Jan. 1993, pp. 88-94.

(56) References Cited

OTHER PUBLICATIONS

McCormick et al., "Characterization of a Cell-Lethal Product from the Photooxidation of Tryptophan: Hydrogen Peroxide", Science, vol. 191, Feb. 6, 1976, pp. 468-469.

McCormick et al., "Near-Ultraviolet Photooxidation of Tryptophan. Proof of Formation of Superoxide Ion", Journal of the American Chemical Society, vol. 100, No. 1, Jan. 4, 1978, pp. 312-313.

Milstein et al., "Hybrid Hybridomas and Their Use in Immunohistochemistry", Nature, vol. 305, Oct. 6, 1983, pp. 537-540.

Morimoto et al., "Single-Step Purification of F(ab')2 Fragments of Mouse Monoclonal Antibodies (Immunoglobulins G1) by Hydrophobic Interaction High Erformance Liquid Chromatography Using TSKgel Phenyl-5PW", Journal of Biochemical and Biophysical Methods, vol. 24, 1992, pp. 107-117.

Morrison et al., "Chimeric Human Antibody Molecules: Mouse Antigen-binding Domains with Human Constant Region Domains", PNAS, vol. 81, Nov. 1984, pp. 6851-6855.

Morrison, Sherie L., "Success in Specification", Nature, vol. 368, Apr. 28, 1994, pp. 812-813.

Munson et al., "Ligand: A Versatile Computerized Approach for Characterization of Ligand-binding Systems", Analytical Biochemistry, vol. 107, 1980, pp. 220-239.

Neuberger, Michael, "Generating High-Avidity Human Mabs in Mice", Nature Biotechnology, vol. 14, Jul. 1996, 1 page.

Ni, Jian, "Research Progress and Future Perspectives in Antibodomics and Antibodomic Drugs", International Antibodomic Drug Industry Research Institute, Xiandai Mianyixue, vol. 26, No. 4, 2006, pp. 265-268.

Orlandi et al., "Cloning Immunoglobulin Variable Domains for Expression by the Polymerase Chain Reaction", Proceedings of the National Academy of Sciences, vol. 86, May 1989, pp. 3833-3837.

Orum et al., "Sequence and Proposed Secondary Structure of the Tetrahymena Therrmophila U3-snRNA", Nucleic Acids Research, vol. 21, No. 10, 1993, pp. 2511.

Pearlman et al., "Analysis of Protein Drugs", Peptide and Protein Drug Delivery, Chapter 6, 1991, 55 pages.

Wurm, F. M. "Production of Recombinant Protein Therapeutics in Cultivated Mammalian Cells," *Nat. Biotechnol.* 22(11):1393-1398, (Nov. 2004).

\* cited by examiner

US 9,441,035 B2

CELL CULTURE MEDIA AND METHODS OF ANTIBODY PRODUCTION

CROSS REFERENCE TO RELATED APPLICATIONS

This application claims the priority benefit of U.S. Provisional Patent Application Ser. No. 61/801,247, filed Mar. 15, 2013, the contents of which are incorporated herein by reference in its entirety.

FIELD OF THE INVENTION

The present invention relates to cell culture media for use in culturing a mammalian cell comprising a nucleic acid encoding bevacizumab, or a fragment thereof, and to methods of using the media in bevacizumab production as well as compositions and kits comprising the bevacizumab, or a fragment thereof, produced by the methods provided herein.

BACKGROUND OF THE INVENTION

Cell culture manufacturing technology is widely used for the production of protein-based therapeutics, such as antibodies, for use in pharmaceutical formulations. Commercial production of protein-based products, such as an antibody product, requires optimization of cell culture parameters in order for the cell to produce enough of the protein product to meet manufacturing demands. However, when cell culture parameters are optimized for improving productivity of the protein product it is also necessary to maintain the desired quality attributes of the product such as the glycosylation profile, aggregate levels, charge heterogeneity, and amino acid sequence integrity (Li, et al., 2010, mAbs., 2(5):466-477).

Bevacizumab, also known as "Avastin®", is a recombinant humanized monoclonal antibody that binds vascular endothelial growth factor in in vitro and in vivo assay systems (U.S. Pat. No. 7,227,004; U.S. Pat. No. 6,884,879; U.S. Pat. No. 7,060,269; U.S. Pat. No. 7,169,901; U.S. Pat. No. 7,297,334) and is used in the treatment of cancer, where it inhibits tumor growth by Hocking the formation of new blood vessels. Bevacizumab has an approximate molecular weight of 149,000 daltons, is glycosylated, and is produced in a mammalian cell (Chinese Hamster Ovary) expression system in a nutrient cell culture medium.

Improved and cost-effective methods of producing bevacizumab, or a fragment thereof, are desirable. Cell culture media comprising components that enable a cell to produce a desired amount of bevacizumab, or a fragment thereof, while maintaining acceptable product quality attributes of bevacizumab, or a fragment thereof, would be beneficial. Cell culture media for use in producing manufacturing-scale amounts of bevacizumab, or a fragment thereof, would be particularly advantageous.

BRIEF SUMMARY OF THE INVENTION

The invention provided herein discloses, inter cilia, methods of producing bevacizumab, or a fragment thereof, in a cell culture medium comprising at least two of copper, insulin, and cystine, and optionally comprises an animal-derived hydrolysate and/or a plant-derived hydrolysate. Also provided are methods for culturing a mammalian cell (e.g., a CHO cell) comprising a nucleic acid encoding bevacizumab, or a fragment thereof, using a cell culture medium provided herein. Further disclosed herein are cell culture media compositions that enhance the amount (e.g., enhance the titer) of bevacizumab, or a fragment thereof, produced from a mammalian cell in cell culture, as well as compositions comprising bevacizumab, or a fragment thereof, produced by the methods described herein.

Accordingly, in one aspect, the invention provides a method of producing bevacizumab, or a fragment thereof, comprising the step of culturing a mammalian cell comprising a nucleic acid encoding bevacizumab or fragment thereof in a cell culture medium, wherein the cell culture medium comprises two or more components selected from the group consisting of copper, insulin, and cystine, and wherein the cell produces bevacizumab, or a fragment thereof. In a further embodiment, the cell culture medium comprises copper and insulin. In another further embodiment, the cell culture medium comprises copper and cystine. In yet another further embodiment, the cell culture medium comprises insulin and cystine. In still another further embodiment, the cell culture medium comprises copper, insulin, and cystine. In any of the embodiments herein, the cell culture medium can further comprise a plant-derived hydrolysate, an animal-derived hydrolysate or both a plant-derived hydrolysate and an animal-derived hydrolysate. In some of the embodiments herein, the cell culture medium comprises copper at a concentration selected from the concentrations listed in Table 1. In some of the embodiments herein, the cell culture medium comprises insulin at a concentration selected from the concentrations listed in Table 1. In some of the embodiments herein, the cell culture medium comprises cystine at a concentration selected from the concentrations listed in Table 1. It is understood that any combination of amounts of copper, insulin and/or cystine, e.g., the amounts provided in Table 1, are intended the same as if each and every combination of amounts were specifically and individually listed. In any of the embodiments herein, the cell culture medium can comprise insulin at a concentration of from about 7.0 mg/L to about 11.0 mg/L. In any of the embodiments herein, the cell culture medium can comprise copper at a concentration of from about 69.0 nM to about 400.0 nM. In any of the embodiments herein, the cell culture medium can comprise cystine at a concentration of from about 0.8 mM to about 2.5 mM. In any of the embodiments herein, the cell culture medium can comprise an animal-derived hydrolysate at a concentration of from about 5.6 g/L to about 38.0 g/L. In any of the embodiments herein, the cell culture medium can comprise a plant-derived hydrolysate at a concentration of from about 1.4 g/L to about 6.2 g/L. In some embodiments herein, the cell culture medium is a basal cell culture medium. In some embodiments herein, the cell culture medium is a feed cell culture medium. In some embodiments herein, the cell culture medium is a basal cell culture medium comprising at least one of copper, insulin, and cystine, and where the basal cell culture medium is supplemented (e.g., at a period of time following initiation of a cell culture cycle, such as any one of at least one time, two times, at least three times, at least four times, at least five times, at least six times, at least seven times, etc. of a cell culture cycle) with a feed cell culture medium comprising any one or more of insulin, an animal-derived hydrolysate and a plant-derived hydrolysate. In another variation, a feed cell culture medium comprises any one or more of insulin, an animal-derived hydrolysate, a plant-derived hydrolysate, cysteine and cystine. In another variation, a feed cell culture medium comprises insulin, an animal-derived hydrolysate, a plant-derived hydrolysate and cysteine. In another variation, a feed cell culture medium comprises any one or more of insulin, an animal-derived hydrolysate, a plant-derived hydrolysate and cystine. The feed cell culture medium may comprise the any one or more of insulin, an animal-derived hydrolysate, a plant-derived hydrolysate, cysteine and cystine in any amount provided herein. In some embodiments herein, the cell culture medium comprises insulin and the method further comprises the step of adding an additional amount of insulin to the cell culture medium (e.g., such as via a feed medium introduced to the basal cell culture medium at a period of time following initiation of the cell culture cycle). In some embodiments, the additional amount of insulin is added in an amount to provide insulin in the cell culture medium at a concentration selected from the concentrations listed in Table 1. In a further embodiment, the additional amount of insulin is added to the cell culture medium at least once during the cell culture cycle. In another further embodiment, the additional amount of insulin is added to the cell culture medium at least three times during the cell culture cycle. In yet another further embodiment, the additional amount of insulin is added to the cell culture medium at least six times during the cell culture cycle. In some of the embodiments herein, the additional amount of insulin is added in an amount to provide insulin in the cell culture medium at a concentration of from about 5.6 mg/L to about 66.0 mg/L. In some of the embodiments herein, the method further comprises the step of adding an additional amount of animal-derived hydrolysate and/or plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and/or plant-derived hydrolysate added to the cell culture is added in an amount to provide animal-derived hydrolysate and/or plant-derived hydrolysate in the cell culture medium at a concentration selected from the concentrations listed in Table 1. In any of the embodiments herein, the cell (e.g., a CHO cell capable of producing bevacizumab, or a fragment thereof) can be cultured at a temperature ranging from about 28° C. to about 37° C. or about 31° C. to about 37° C. In any of the embodiments herein, bevacizumab, or a fragment thereof, can be secreted into the cell culture medium. In any of the embodiments herein, the method can further comprise the step of recovering the bevacizumab, or a fragment thereof, from the cell culture. In a particular variation, the recovered bevacizumab is purified.

Also provided herein are methods of producing bevacizumab, or a fragment thereof, in a cell culture medium comprising an animal-derived hydrolysate and a plant-derived hydrolysate and optionally further comprising copper, insulin and/or cystine. In one such aspect, the an animal-derived hydrolysate is present in a greater amount than the plant-derived hydrolysate. In one such variation, the animal-derived hydrolysate is present in the cell culture media at a concentration of from about 5.6 g/L to about 38.0 g/L or from about 7.0 g/L to about 35.0 g/L or from about 7.0 g/L to about 25.0 g/L or from about 7.0 g/L to about 15.0 g/L or from about 8.0 g/L to about 12.0 g/L or from about 7.0 g/L to about 11.0 g/L or about any one of 5 g/L, 10 g/L, 15 g/L, 20 g/L, 25 g/L, 30 g/L, 35 g/L, 40 g/L, 45 g/L or 50 g/L or about any one of 5 g/L, 6 g/L, 7 g/L, 8 g/L, 9 g/L, 10 g/L, 11 g/L, or 12 g/L or about 10 g/L. In another variation, the plant-derived hydrolysate is present in the cell culture media at a concentration of from about 1.4 g/L to about 6.2 g/L or from about 1.5 g/L to about 5.5 g/L or from about 1.5 g/L to about 4.5 g/L or from about 1.5 g/L to about 3.5 g/L or from about 1.5 g/L to about 2.5 g/L or from about 1.75 g/L to about 2.75 g/L or from about 2.0 g/L to about 3.0 g/L or from about 2.25 g/L to about 2.75 g/L or about any one of 1.75 g/L, 2.0 g/L, 2.25 g/L, 2.5 g/L, 3.0 g/L, 3.25, 3.5 g/L, 3.75 g/L, or 4.0 g/L or about any one of 2.0 g/L, 2.25 g/L, 2.5 g/L or 3.0 g/L or about 2.5 g/L. It is understood that each and every combination of amount of animal-derived hydrolysate and plant-derived hydrolysate is described the same as if each and every combination were specifically and individually listed.

In some aspects, the invention provides bevacizumab, or fragment thereof, produced by any of the methods described herein.

In other aspects, the invention provides a composition comprising: (i) bevacizumab, or a fragment thereof, produced by any of the methods described herein and (ii) a pharmaceutically acceptable carrier.

In some aspects, the invention also provides a method of culturing a mammalian cell comprising a nucleic acid encoding bevacizumab, or a fragment thereof, the method comprising the step of contacting the mammalian cell with a cell culture medium comprising two or more components selected from the group consisting of copper, insulin and cystine. In a further embodiment, the cell culture medium comprises copper and insulin. In another further embodiment, the cell culture medium comprises copper and cystine. In yet another further embodiment, the cell culture medium comprises insulin and cystine. In still yet another further embodiment, the cell culture medium comprises copper, insulin, and cystine. In some embodiments herein, the cell culture medium further comprises a plant-derived hydrolysate, an animal-derived hydrolysate or both a plant-derived hydrolysate and an animal-derived hydrolysate. In some of the embodiments herein, the cell culture medium comprises insulin at a concentration of from about 7.0 mg/L to about 11.0 mg/L. In some of the embodiments herein, the cell culture medium comprises copper at a concentration of from about 69.0 nM to about 400.0 nM. In some of the embodiments herein, the cell culture medium comprises cystine at a concentration of from about 0.8 mM to about 2.5 mM. In some of the embodiments herein the cell culture medium comprises an animal-derived hydrolysate at a concentration of from about 5.6 g/L to about 38.0 g/L. In some of the embodiments herein, the cell culture medium comprises a plant-derived hydrolysate at a concentration of from about 1.4 g/L to about 6.2 g/L. In some of the embodiments herein, the cell culture medium is a basal cell culture medium. In some embodiments herein, the cell culture medium is a feed cell culture medium. In some embodiments herein, the cell culture medium is a basal cell culture medium comprising at least one of copper, insulin, and cystine, and where the basal cell culture medium is supplemented (e.g., at a period of time following initiation of a cell culture cycle, such as any one of at least two times, at least three times, at least four times, at least five times, at least six times, at least seven times, etc. of a cell culture cycle) with a feed cell culture medium comprising any one or more of insulin, an animal-derived hydrolysate and a plant-derived hydrolysate. In some embodiments herein, the cell culture medium comprises insulin and the method further comprises the step of adding an additional amount of insulin to the cell culture medium. In a further embodiment, the additional amount of insulin is added to the cell culture medium at least once during the cell culture cycle. In another further embodiment, the additional amount of insulin is added to the cell culture medium at least three times during the cell culture cycle. In yet another further embodiment, the additional amount of insulin is added to the cell culture medium at least six times during the cell culture cycle. In some embodiments, the additional amount of insulin is added in an amount to provide insulin in the cell culture medium at a concentration of from about 5.6 mg/L to about 66.0 mg/L. In some of the embodiments herein, the method further comprises the step of adding an additional amount of animal-derived hydrolysate and/or plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and/or plant-derived hydrolysate added to the cell culture is added in an amount to provide animal-derived hydrolysate and/or plant-derived hydrolysate in the cell culture medium at a concentration selected from the concentrations listed in Table 1. In some of the embodiments herein, the cell is cultured at a temperature ranging about 28° C. to about 37° C. or from about 31° C. to about 37° C. In any of the embodiments herein, bevacizumab, or a fragment thereof, can be secreted into the cell culture medium. In some embodiments herein, the mammalian cell is contacted with the cell culture medium during the cell's growth phase. In some embodiments herein, the mammalian cell is contacted with the cell culture medium during the cell's production phase.

In other aspects, the invention provides a kit for supplementing a cell culture medium for use in culturing a mammalian cell comprising a nucleic acid encoding bevacizumab, or a fragment thereof, the kit comprising at least two of components (i)-(iii): (i) insulin in an amount to provide from about 7.0 mg/L to about 11.0 mg/L insulin in the cell culture medium; (ii) cystine in an amount to provide from about 0.8 mM to about 2.5 mM cystine in the cell culture medium; (iii) and copper in an amount to provide from about 25.0 nM to about 400.0 nM copper in the cell culture medium. In some embodiments, the kit further comprises a plant-derived hydrolysate. In a further embodiment, the kit comprises the plant-derived hydrolysate in an amount to provide from about 1.4 g/L to about 6.2 g/L plant-derived hydrolysate in the cell culture medium. In any of the embodiments herein, the kit can further comprise an animal-derived hydrolysate. In some embodiments, the kit comprises the animal-derived hydrolysate in an amount to provide from about 5.6 g/L to about 38.0 g/L animal-derived hydrolysate in the cell culture medium. The kit may additionally contain instructions for use, such as instructions for use in supplementing a cell culture medium.

In another aspect, the invention provides a cell culture medium for use in culturing a mammalian cell comprising a nucleic acid encoding bevacizumab, or a fragment thereof, the cell culture medium comprising at least two of components (i)-(iii): (i) from about 7.0 mg/L to about 11.0 mg/L insulin; (ii) from about 25.0 nM to about 400.0 nM copper; and (iii) from about 0.8 mM to about 2.5 mM cystine. In some embodiments, the cell culture medium comprises from about 7.0 mg/L to about 11.0 mg/L insulin; and from about 25.0 nM to about 400.0 nM copper. In some embodiments, the cell culture medium comprises: from about 7.0 mg/L to about 11.0 mg/L insulin; and from about 0.8 mM to about 2.5 mM cystine. In some embodiments, the cell culture medium comprises from about 25.0 nM to about 400.0 nM copper; and from about 0.8 mM to about 2.5 mM cystine. In any of the embodiments herein, the cell culture medium can further comprise from about 1.4 g/L to about 6.2 g/L plant-derived hydrolysate. In any of the embodiments herein, the cell culture medium can further comprise from about 5.6 g/L to about 38.0 g/L animal-derived hydrolysate.

In yet another aspect, the invention also provides a composition comprising (a) a mammalian cell comprising a nucleic acid encoding bevacizumab, or a fragment thereof; and (b) any cell culture medium provided herein.

In another aspect, the invention provides a composition comprising: (a) bevacizumab, or a fragment thereof; and (b) any cell culture medium provided herein. In a further embodiment, bevacizumab, or a fragment thereof, is secreted into the medium by a mammalian cell comprising a nucleic acid encoding bevacizumab, or a fragment thereof.

In some aspects, also provided herein is a method of enhancing titer of bevacizumab, or a fragment thereof, from a mammalian cell comprising a nucleic acid encoding bevacizumab, or a fragment thereof, the method comprising the step of culturing the mammalian cell in a cell culture medium comprising at least two of insulin, copper and cystine, wherein titer is enhanced relative to culturing the mammalian cell in a cell culture medium without at least two of insulin, copper and cystine. In some embodiments, the cell culture medium comprises copper and insulin. In some embodiments, the cell culture medium comprises copper and cystine. In some embodiments, the cell culture medium comprises insulin and cystine. In some embodiments, the cell culture medium comprises copper, insulin, and cystine. In any of the embodiments herein, the cell culture medium can further comprise a plant-derived hydrolysate, an animal-derived hydrolysate or both a plant-derived hydrolysate and an animal-derived hydrolysate. In any of the embodiments herein, the cell culture medium can comprise insulin at a concentration of from about 7.0 mg/L to about 11.0 mg/L. In any of the embodiments herein, the cell culture medium can comprise copper at a concentration of from about 69.0 nM to about 400.0 nM. In any of the embodiments herein, the cell culture medium can comprise cystine at a concentration of from about 0.8 mM to about 2.5 mM. In any of the embodiments herein, the cell culture medium can comprise an animal-derived hydrolysate at a concentration of from about 5.6 g/L to about 38.0 g/L. In any of the embodiments herein, the cell culture medium can comprise a plant-derived hydrolysate at a concentration of from about 1.4 g/L to about 6.2 g/L. In some embodiments, the cell culture medium is a basal cell culture medium. In some embodiments herein, the cell culture medium is a feed cell culture medium. In some embodiments herein, the cell culture medium is a basal cell culture medium comprising at least one of copper, insulin, and cystine, and where the basal cell culture medium is supplemented (e.g., at a period of time following initiation of a cell culture cycle, such as any one of at least two times, at least three times, at least four times, at least five times, at least six times, at least seven times, etc. of a cell culture cycle) with a feed cell culture medium comprising any one or more of insulin, an animal-derived hydrolysate and a plant-derived hydrolysate. In some embodiments, the cell culture medium comprises insulin and the method further comprises the step of adding an additional amount of insulin to the cell culture medium. In a further embodiment, the additional amount of insulin is added to the cell culture medium at least once during the cell culture cycle. In another further embodiment, the additional amount of insulin is added to the cell culture medium at least three times during the cell culture cycle. In yet another further embodiment, the additional amount of insulin is added to the cell culture medium at least six times during the cell culture cycle. In some embodiments herein, the additional amount of insulin is added in an amount to provide insulin in the cell culture medium at a concentration of from about 5.6 mg/L to about 66.0 mg/L. In some embodiments herein, the method further comprises the step of adding an additional amount of animal-derived hydrolysate and/or plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and/or plant-derived hydrolysate added to the cell culture is added in an amount to provide animal-derived hydrolysate and/or plant-derived hydrolysate in the cell culture medium at a concentration selected from the concentrations listed in Table 1. In any of the embodiments herein, the cell may be cultured at a temperature ranging from about 28° C. to about 37° C. or from about 31° C. to about 37° C. In any of the embodiments herein, bevacizumab, or a fragment thereof, can be secreted into the cell culture medium. In any of the embodiments herein, the method may further comprise the step of recovering the bevacizumab, or a fragment thereof, from the cell culture. In a further aspect, the recovered bevacizumab, or a fragment thereof, is purified.

In another aspect, the invention herein provides a method of culturing a mammalian cell comprising a nucleic acid encoding bevacizumab, or a fragment thereof, in a cell culture medium comprising at least two of insulin, copper and cystine, wherein titer of bevacizumab, or a fragment thereof, is enhanced relative to culturing the mammalian cell in a cell culture medium without at least two of insulin, copper and cystine. In some embodiments, the cell culture medium comprises copper and insulin. In some embodiments, the cell culture medium comprises copper and cystine. In some embodiments, the cell culture medium comprises insulin and cystine. In some embodiments, the cell culture medium comprises copper, insulin, and cystine. In some of the embodiments herein, the cell culture medium further comprises a plant-derived hydrolysate, an animal-derived hydrolysate or both a plant-derived hydrolysate and an animal-derived hydrolysate. In some of the embodiments herein, the cell culture medium comprises insulin at a concentration of from about 7.0 mg/L to about 11.0 mg/L. In some of the embodiments herein, the cell culture medium comprises copper at a concentration of from about 69.0 nM to about 400.0 nM. In some of the embodiments herein, the cell culture medium comprises cystine at a concentration of from about 0.8 mM to about 2.5 mM. In some of the embodiments herein, the cell culture medium comprises an animal-derived hydrolysate at a concentration of from about 5.6 g/L to about 38.0 g/L. In some of the embodiments herein, the cell culture medium comprises a plant-derived hydrolysate at a concentration of from about 1.4 g/L to about 6.2 g/L. In some embodiments, the cell culture medium is a basal cell culture medium. In some embodiments herein, the cell culture medium is a feed cell culture medium. In some embodiments herein, the cell culture medium is a basal cell culture medium comprising at least one of copper, insulin, and cystine, and where the basal cell culture medium is supplemented (e.g., at a period of time following initiation of a cell culture cycle, such as any one of at least two times, at least three times, at least four times, at least five times, at least six times, at least seven times, etc. of a cell culture cycle) with a feed cell culture medium comprising any one or more of insulin, an animal-derived hydrolysate and a plant-derived hydrolysate. In any of the embodiments herein, the cell culture medium can comprise insulin and the method can further comprise the step of adding an additional amount of insulin to the cell culture medium. In a further embodiment, the additional amount of insulin is added to the cell culture medium at least once during the cell culture cycle. In another further embodiment, the additional amount of insulin is added to the cell culture medium at least three times during the cell culture cycle. In yet another further embodiment, the additional amount of insulin is added to the cell culture medium at least six times during the cell culture cycle. In some of the embodiments herein, the additional amount of insulin is added in an amount to provide insulin in the cell culture medium at a concentration of from about 5.6 mg/L to about 66.0 mg/L. In some of the embodiments herein, the method further comprises the step of adding an additional amount of animal-derived hydrolysate and/or plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and/or plant-derived hydrolysate added to the cell culture is added in an amount to provide animal-derived hydrolysate and/or plant-derived hydrolysate in the cell culture medium at a concentration selected from the concentrations listed in Table 1. In some of the embodiments herein, the cell is cultured at a temperature ranging from about 28° C. to about 37° C. or from about 31° C. to about 37° C., such as a temperature of about 31° C., 33° C. or 35° C. It is understood that the temperature may vary (either up or down) throughout the cell culture process, e.g., within a temperature ranging from about 28° C. to about 37° C. In one aspect, the cell is cultured at a first temperature of about 35° C. for a first period of time (such as about 1-10 or 1-8 or 1-7 days), is cultured at a second temperature of about 33° C. for a second period of time (such as about 1-5 or 1-4 or 1-3 or 1-2 days), and is cultured at a third temperature of about 31° C. for a third period of time (such as about 1-5 or 1-4 or 1-3 or 1-2 days). In any of the embodiments herein, bevacizumab, or a fragment thereof, can be secreted into the cell culture medium. In some embodiments, the method further comprises the step of recovering the bevacizumab, or a fragment thereof, from the cell culture. In one aspect, the recovered bevacizumab, or a fragment thereof, is purified.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

DETAILED DESCRIPTION

Improved and cost-effective methods of producing bevacizumab, or a fragment thereof, are provided. Cell culture media comprising components that enable a cell to consistently produce a desired amount of bevacizumab, or a fragment thereof, while maintaining acceptable product quality attributes of bevacizumab, or a fragment thereof, are described. The cell culture media provided herein may find use in producing manufacturing-scale amounts of bevacizumab, or a fragment thereof.

The methods provided herein, including: (i) a method of producing bevacizumab, or a fragment thereof; (ii) a method of culturing a mammalian cell comprising a nucleic acid encoding bevacizumab, or a fragment thereof; and (iii) a method of enhancing production of bevacizumab, or a fragment thereof, (e.g., enhancing titer yields of bevacizumab, or a fragment thereof) from a mammalian cell comprising a nucleic acid encoding bevacizumab, or a fragment thereof, in one aspect utilize a cell culture medium comprising two or more of copper, insulin, and cystine (such as a cell culture medium comprising copper and insulin, or a cell culture medium comprising copper and cystine, or a cell culture medium comprising insulin and cystine, or a cell culture medium comprising copper, insulin and cystine). Bevacizumab, or fragment thereof, produced by any of the methods detailed herein is also provided, as are compositions comprising bevacizumab, or fragment thereof. In one aspect, bevacizumab, or fragment thereof, produced by any of the methods detailed herein exhibits acceptable product quality attributes of bevacizumab, or a fragment thereof, such as N-glycosylation profile, charge heterogeneity, and sequence integrity. In a particular variation, the product quality attributes of bevacizumab, or a fragment thereof, are acceptable if they are substantially similar to bevacizumab, or a fragment thereof produced by a method that does not use a cell culture medium comprising at least two of copper, insulin, and cystine. A cell culture medium comprising two or more of copper, insulin, and cystine (e.g., a cell culture medium comprising: (i) copper and insulin; (ii) copper and cystine; (iii) insulin and cystine; or (iv) copper, insulin and cystine) is also provided. In one variation, the cell culture medium comprising two or more of copper, insulin, and cystine enhances production of bevacizumab, or a fragment thereof, (e.g., enhances titer yields of bevacizumab, or a fragment thereof) by a mammalian cell cultured in the medium relative to culturing the mammalian cell in a cell culture medium without at least two of insulin, copper and cystine. Also provided herein is a composition comprising a cell culture medium comprising at least two of copper, insulin, and cystine and (i) a mammalian cell comprising a nucleic acid encoding bevacizumab, or a fragment thereof and/or (ii) bevacizumab, or a fragment thereof. A culturing vessel comprising any of the cell culture media provided herein are provided. In one aspect, the culturing vessel is a manufacturing scale culturing vessel, such as a culturing vessel capable of containing at least 2 liters, at least 10 liters, at least 100 liters, at least 500 liters, at least 1,000 liters, at least 2,500 liters, at least 5,000 liters, at least 7,500 liters, at least 10,000 liters, at least 12,000 liters or more of a cell culture medium provided herein as is required for producing manufacturing scale amounts of bevacizumab from cell culture. Thus, the methods provided herein may find use in a manufacturing-scale production of bevacizumab, or a fragment thereof.

I. Definitions

The term "bevacizumab" refers to a recombinant humanized anti-VEGF monoclonal antibody generated according to Presta et al. (1997) Cancer Res. 57:4593-4599, also known as "rhuMAb VEGF" or "AVASTIN®". It comprises mutated human IgG1 framework regions and antigen-binding complementarity-determining regions from the murine anti-human VEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. bevacizumab binds to the same epitope as the monoclonal anti-VEGF antibody A4.6.1 produced by hybridoma ATCC HB 10709. Bevacizumab and other humanized anti-VEGF antibodies are further described in U.S. Pat. No. 6,884,879.

The terms "medium" and "cell culture medium" refer to a nutrient source used for growing or maintaining cells. As is understood by a person of skill in the art, the nutrient source may contain components required by the cell for growth and/or survival or may contain components that aid in cell growth and/or survival. Vitamins, essential or non-essential amino acids (e.g., cysteine and cystine), and trace elements (e.g., copper) are examples of medium components. Any media provided herein may also be supplemented with any one or more of insulin, plant hydrolysates and animal hydrolysates.

"Culturing" a cell refers to contacting a cell with a cell culture medium under conditions suitable to the survival and/or growth and/or proliferation of the cell.

"Batch culture" refers to a culture in which all components for cell culturing (including the cells and all culture nutrients) are supplied to the culturing vessel at the start of the culturing process.

"Fed batch cell culture," as used herein refers to a batch culture wherein the cells and culture medium are supplied to the culturing vessel initially, and additional culture nutrients are fed, continuously or in discrete increments, to the culture during the culturing process, with or without periodic cell and/or product harvest before termination of culture.

"Perfusion culture" is a culture by which the cells are restrained in the culture by, e.g., filtration, encapsulation, anchoring to microcarriers, etc., and the culture medium is continuously or intermittently introduced and removed from the culturing vessel.

"Culturing vessel" refers to a container used for culturing a cell. The culturing vessel can be of any size so long as it is useful for the culturing of cells.

The term "titer" as used herein refers to the total amount of recombinantly expressed antibody produced by a cell culture divided by a given amount of medium volume. Titer is typically expressed in units of milligrams of antibody per milliliter of medium. Titer can be expressed or assessed in terms of a relative measurement, such as a percentage increase in titer as compared obtaining the protein product under different culture conditions.

A "nucleic acid" refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

An "isolated nucleic acid" means and encompasses a non-naturally occurring, recombinant or a naturally occurring sequence outside of or separated from its usual context. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the protein where, for example, the nucleic acid molecule is in a chromosomal location different from that of natural cells.

An "isolated" protein (e.g., an isolated antibody) is one which has been identified and separated and/or recovered from a component of its natural environment. Contaminant components of its natural environment are materials which would interfere with research, diagnostic or therapeutic uses for the protein, and may include enzymes, hormones, and other proteinaceous or nonproteinaceous solutes. Isolated protein includes the protein in situ within recombinant cells since at least one component of the protein's natural environment will not be present. Ordinarily, however, isolated protein will be prepared by at least one purification step.

A "purified" protein (e.g., antibody) means that the protein has been increased in purity, such that it exists in a form that is more pure than it exists in its natural environment and/or when initially produced and/or synthesized and/or amplified under laboratory conditions. Purity is a relative term and does not necessarily mean absolute purity.

"Contaminants" refer to materials that are different from the desired protein product (e.g., different from an antibody product). A contaminant may include, without limitation: host cell materials, such as CHOP; nucleic acid; a variant, fragment, aggregate or derivative of the desired protein; another polypeptide; endotoxin; viral contaminant; cell culture media components, etc.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. An antibody can be human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., Springer-Verlag, New York, pp. 269-315, 1994.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc.*

Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, inMethods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

"Pharmaceutically acceptable" carriers, excipients, or stabilizers are ones which are nontoxic to the cell or mammal being exposed thereto at the dosages and concentrations employed (Remington's Pharmaceutical Sciences (20$^{th}$ edition), ed. A. Gennaro, 2000, Lippincott, Williams & Wilkins, Philadelphia, Pa.). Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™.

A "sterile" formulation is aseptic or free or essentially free from all living microorganisms and their spores.

As used in this specification and the appended claims, the singular forms "a", "an" and "the" include plural referents unless the content clearly dictates otherwise. Thus, for example, reference to "a compound" optionally includes a combination of two or more such compounds, and the like.

It is understood that aspects and embodiments of the invention described herein include "comprising," "consisting," and "consisting essentially of" aspects and embodiments.

Reference to "about" a value or parameter herein includes (and describes) embodiments that are directed to that value or parameter per se. For example, description referring to "about X" includes description of "X." Numeric ranges are inclusive of the numbers defining the range.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

II. Cell Culture Media

Cell culture media provided herein may find use in methods (e.g., a method of producing bevacizumab, or a fragment thereof; a method of culturing a mammalian cell comprising a nucleic acid encoding bevacizumab, or a fragment thereof; and/or a method of enhancing production of bevacizumab, or a fragment thereof, such as by enhancing titer yields of bevacizumab, from a mammalian cell comprising a nucleic acid encoding bevacizumab) and in compositions (e.g., a composition comprising a cell culture medium comprising at least two of copper, insulin, and cystine and (i) a mammalian cell comprising a nucleic acid encoding bevacizumab, or a fragment thereof and/or (ii) bevacizumab, or a fragment thereof) as detailed herein.

In some aspects, the cell culture medium provided herein comprises components (e.g., at least two of copper, insulin, and cystine) that may be used in culturing a cell that produces bevacizumab, or a fragment thereof, wherein the cell, when cultured in the presence of the media components (e.g., at least two of copper, insulin, and cystine), produces bevacizumab, or a fragment thereof, in a desired amount, which may be in an amount that is greater than the amount of bevacizumab produced by a cell cultured in a cell culture medium that does not contain the media components (e.g., a cell culture medium that does not contain at least two of copper, insulin, and cystine). In one aspect, the cell culture media provided herein is used in culturing a cell that produces bevacizumab, or a fragment thereof, wherein the cell, when cultured in the presence of the media components (e.g., at least two of copper, insulin, and cystine), produces bevacizumab, or a fragment thereof, in a desired amount and with an acceptable quality attribute, such as an acceptable molecular weight. As used herein, "an acceptable quality attribute" of bevacizumab can refer to a chemical and/or physical attribute required for regulatory approval or marketing of bevacizumab and may be the chemical and/or physical attribute used in assessing lot-to-lot consistency of batches of bevacizumab, or a fragment thereof, produced by a cell.

In other aspects of the invention, cell culture media components (e.g., at least two of copper, insulin, and cystine) have been identified as capable of providing antibody-producing cells with improved or acceptable quality attributes that contribute to higher production of bevacizumab (e.g., results in higher titer of bevacizumab) as compared to cells that produce bevacizumab and are cultured in a cell culture medium that does not contain these components (a cell culture medium that does not contain at least two of copper, insulin and cystine). Certain identified media components (e.g., at least two of copper, insulin, and cystine) can be used to provide an antibody-producing cell (e.g., a CHO cell) with the capability of producing bevacizumab, or a fragment thereof, with an acceptable titer, which in one aspect is a titer greater than the titer obtained when the cells produce bevacizumab, or a fragment thereof, in a cell culture medium that does not comprise at least two of copper, insulin, and cystine. As used herein, "an acceptable titer" of an antibody produced from a cultured cell (e.g., bevacizumab produced from a CHO cell) can as a non-limiting example refer to the amount of antibody required to meet manufacturing-scale production of the antibody or to the amount of antibody required to assess consistency in lot-to-lot batches of the antibody product. The cell culture media provided herein may improve the amount of bevacizumab that is produced from a cell comprising a nucleic acid encoding bevacizumab as compared to the amount of bevacizumab produced from the cell cultured in a different media.

A cell culture medium for use in culturing a cell for use in culturing a mammalian cell comprising a nucleic acid encoding bevacizumab, or a fragment thereof, is provided, wherein the cell culture medium comprises any one or more of: (a) copper; (b) insulin; (c) cystine; (d) an animal-derived hydrolysate; and (e) a plant-derived hydrolysate. In some embodiments, the cell culture medium comprises 2 or 3 or 4 or 5 of components (a), (b), (c), (d) and (e). It is understood that the cell culture medium provided herein may contain any combination of components (a), (b), (c), (d) and (e) the same as if each and every combination were specifically and individually listed. For example, it is understood that a cell culture medium comprising three of components (a), (b), (c), (d) and (e) may comprise any combination of the components so long as at least three of the components are present (e.g., a cell culture medium comprising components (a), (b) and (c) or comprising components (a), (d) and (e) or comprising components (c), (d) and (e) are contemplated). In some embodiments, a cell culture medium provided herein comprises components (a), (b), (c), (d) and (e). In some embodiments, a cell culture medium provided herein comprises (a) and (b). In some embodiments, a cell culture medium provided herein comprises (a) and (c). In some embodiments, a cell culture medium provided herein comprises (b) and (c).

In some aspects, a cell culture medium as provided herein contains one or more media components selected from the group consisting of copper, insulin, cystine in amounts as described in Table 1. In some embodiments, the cell culture medium further comprises an animal-derived hydrolysate in amounts as described in Table 1. In other embodiments, the cell culture medium further comprises a plant-derived hydrolysate in amounts as described in Table 1. In some embodiments, the cell culture medium further comprises both an animal-derived hydrolysate and a plant-derived hydrolysate in amounts as described in Table 1.

It is also understood that a cell culture medium provided herein may comprise any one or more of the cell culture medium components of Table 1 (any one or more of copper, insulin, cystine, an animal-derived hydrolysate and a plant-derived hydrolysate) in any of the amounts listed in Table 1, the same as if each and every combination of components and amounts were specifically and individually listed. In one variation, the cell culture medium provided herein comprises two or three or four or each of copper, insulin, cystine, an animal-derived hydrolysate and a plant-derived hydrolysate in any of the amounts listed in Table 1, the same as if each and every combination of components and amounts were specifically and individually listed. In one aspect, the cell culture medium comprises at least two of copper, insulin and cystine in any of the amounts listed in Table 1, and an in further variation further comprises an animal-derived hydrolysate and/or a plant-derived hydrolysate in any of the amounts listed in Table 1.

TABLE 1

Exemplary Amounts of Media Components

| Component | Amount of Component in Medium |
| --- | --- |
| (a) Insulin | from about 1.0 mg/L to about 100.0 mg/L; from about 5.0 mg/L to about 80.0 mg/L; from about 5.0 mg/L to about 60.0 mg/L; from about 5.0 mg/L to about 50.0 mg/L; from about 5.0 mg/L to about 40.0 mg/L; from about 5.0 mg/L to about 30.0 mg/L; from about 5.0 mg/L to about 25.0 mg/L; from about 10.0 mg/L to about 25.0 mg/L; from about 10.0 mg/L to about 30.0 mg/L; from about 15.0 mg/L to about 20.0 mg/L; from about 5.0 mg/L to about 15.0 mg/L; from about 6.0 mg/L to about 12.0 mg/L; from about 7.0 mg/L to about 11.0 mg/L; from about 8.0 mg/L to about 10.0 mg/L; from about 10 mg/L to about 100 mg/L; from about 10 mg/L to about 50 mg/L; from about 10 mg/L to about 35 mg/L; from about 10 mg/L to about 250 mg/L; from about 1.0 mg/L to about 66 mg/L; from about 1.0 mg/L to about 60 mg/L; from about 1.0 mg/L to about 50 mg/L; from about 1.0 mg/L to about 40 mg/L; from about 1.0 mg/L to about 30 mg/L; from about 1.0 mg/L to about 20 mg/L; from about 1.0 mg/L to about 10 mg/L; from about 10 mg/L to about 66 mg/L; from about 20 mg/L to about 66 mg/L; from about 30 mg/L to about 66 mg/L; from about 40 mg/L to about 66 mg/L; from about 50 mg/L to about 66 mg/L; from about 60 mg/L to about 66 mg/L; from about 5.6 mg/L to about 66 mg/L; from about 10 mg/L to about 60 mg/L; from about 20 mg/L to about 50 mg/L; from about 30 mg/L to about 40 mg/L; from about 1 mg/L to about 14 mg/L; from about 1.3 mg/L to about 13 mg/L; from about 1.6 mg/L to about 12 mg/L; from about 1.4 mg/L to about 11 mg/L; from about 5.6 mg/L to about 14 mg/L; from about 5.9 mg/L to about 13 mg/L; from about 6.2 mg/L to about 12 mg/L; from about 7 mg/L to about 11 mg/L; about any of 1.0 or 2.0 or 3.0 or 4.0 or 5.0 or 6.0 or 7.0 or 8.0 or 9.0 or 10 or 11 or 12 or 13 or 14 or 15 or 16 or 17 or 18 or 19 or 20 or 21 or 22 or 23 or 24 or 25 or 26 or 27 or 27 or 28 or 29 or 30 or 31 or 32 or 33 or 34 or 35 or 36 or 37 or 38 or 39 or 40 or 41 or 42 or 43 or 45 mg/L; any of 5.6 mg/L, 6 mg/L, 6.2 mg/L, 7 mg/L, 8 mg/L, 9 mg/L, 10 mg/L, 11 mg/L, 12 mg/L, 13 mg/L, 14 mg/L or 15 mg/L or 16 mg/L or 17 mg/L or 18 mg/L or 19 mg/L or 20 mg/L or 21 mg/L or 22 mg/L or 23 mg/L or 24 mg/L or 25 mg/L; at least about any of 1.0 or 3.0 or 5.0 or 7.0 or 10 or 11 or 12 or 13 or 14 or 15 or 16 or 17 or 18 or 19 or 20 mg/L and no more than about 44 or 24 or 14 or 11 mg/L. |
| (b) Cystine | from about 0.5 mM to about 2.5 mM; from about 0.5 mM to about 2.0 mM; from about 0.5 mM to about 1.75 mM; from about 0.5 mM to about 2.5 mM; from about 0.8 mM to about 2.5 mM; from about 0.8 mM to about 2.25 mM; from about 0.8 mM to about 2.0 mM; from about 0.8 mM to about 1.75 mM; from about 0.8 mM to about 1.6 mM; from about 0.8 mM to about 1.25 mM; from about 0.8 mM to about 1.0 mM; from about 1.0 mM to about 1.6 mM; from about 1.0 mM to about 2.5 mM; from about 1.25 mM to about 2.5 mM; from about 1.5 mM to about 2.5 mM; from about 1.75 mM to about 2.5 mM; from about 2.0 mM to about 2.5 mM; from about 2.25 mM to about 2.5 mM; from about 0.9 mM to about 2.0 mM; from about 0.8 mM to about 1.75 mM; from about 0.9 mM to about 1.5 mM; from about 1.0 mM to about 1.25 mM; from about 1.0 mM to about 2.0 mM; from about 1.0 mM to about 1.5 mM; from about 1.2 mM to about 1.4 mM; about any of 0.8 or 0.9 or 1.0 or 1.1 or 1.2 or 1.3 or 1.4 or 1.5 or 1.6 mM; any of 0.8 mM, 0.85 mM, 0.9 mM, 0.95 mM, 1.0 mM, 1.05 mM, 1.1 mM, 1.15 mM, 1.2 mM, 1.25 mM, 1.3 mM, 1.35 mM, 1.4 mM, 1.5 mM, 1.55 mM, 1.6 mM, 1.65 mM, 1.7 mM, or 1.75 mM; at least about any of 0.8 or 0.9 or 1.0 or 1.1 mM and no more than about 1.75 or 1.6 or 1.5 or 1.4 mM. |
| (c) Copper | from about 69 nM to about 1,000.0 nM; from about 20 nM to about 480.0 nM; from about 20 nM to about 400 nM; from about 20 nM to about 350 nM; from about 20 nM to about 300 nM; from about 20 nM to about 250 nM; from about 20 nM to about 200 nM; from about 20 nM to about 150 nM; from about 20 nM to about 100 nM; from about 20 nM to about 50 nM; from about 50 nM to about 480 nM; |

TABLE 1-continued

Exemplary Amounts of Media Components

| Component | Amount of Component in Medium |
|---|---|
| | from about 100 nM to about 480 nM; from about 150 nM to about 480 nM; from about 200 nM to about 480 nM; from about 250 nM to about 480 nM; from about 300 nM to about 480 nM; from about 325 nM to about 375 nM; from about 350 nM to about 480 nM; from about 400 nM to about 480 nM; from about 50 nM to about 450 nM; from about 100 nM to about 400 nM; from about 150 nM to about 350 nM; from about 200 nM to about 300 nM; from about 22 nM to about 440 nM; from about 26 nM to about 400 nM; from about 30 nM to about 360 nM; from about 54 nM to about 480 nM; from about 62 nM to about 440 nM; from about 69 nM to about 400 nM; from about 80 nM to about 400 nM; from about 100 nM to about 400 nM; from about 125 nM to about 400 nM; from about 150 nM to about 400 nM; from about 200 nM to about 400 nM; from about 250 nM to about 400 nM; from about 300 nM to about 400 nM; from about 325 nM to about 375 nM; from about 325 nM to about 350 nM; any of about 25 or 26 or 27 or 28 or 29 or 30 or 40 or 50 or 60 or 69 or 100 or 110 or 120 or 125 or 130 or 140 or 150 or 160 or 170 or 175 or 180 or 190 or 200 or 210 or 220 or 225 or 230 or 240 or 250 or 260 or 270 or 275 or 280 or 290 or 300 or 310 or 320 or 325 or 330 or 335 or 336 or 337 or 338 or 339 or 340 or 345 or 350 or 360 or 370 or 375 or 380 or 390 or 400 nM; any of 54 nM, 56 nM, 58 nM, 60 nM, 62 nM, 64 nM, 66 nM, 68 nM, 69 nM, 70 nM, 71 nM, 72 nM, 73 nM, 74 nM, 75 nM, 100 nM, 125 nM, 150 nM, 175 nM, 200 nM, 225 nM, 250 nM, 275 nM, 300 nM, 325 nM, 350 nM, 375 nM, or 400 nM; at least any of about 20 or 25 or 30 or 35 or 40 or 45 or 50 or 55 or 60 or 65 or 70 or 80 nM and no more than about 420 or 400 or 380 or 360 nM. |
| (d) Animal-derived hydrolysate | from about 6.0 g/L to about 20 g/L; from about 5.6 g/L to about 38 g/L; from about 5.6 g/L to about 30 g/L; from about 5.6 g/L to about 25 g/L; from about 5.6 g/L to about 20 g/L; from about 7.0 g/L to about 20 g/L; from about 9.0 to about 11.0 g/L; from about 5.6 g/L to about 10 g/L; from about 5.6 to about 38 g/L; from about 10 g/L to about 38 g/L; from about 15 g/L to about 38 g/L; from about 20 g/L to about 38 g/L; from about 25 g/L to about 38 g/L; from about 30 g/L to about 38 g/L; from about 35 g/L to about 38 g/L; from about 10 g/L to about 30 g/L; from about 15 g/L to about 25 g/L; from about 5.6 g/L to about 14 g/L; from about 5.9 g/L to about 13 g/L; from about 6.2 g/L to about 12 g/L; from about 7.0 g/L to about 11.0 g/L; from about 7.0 g/L to about 35.0 g/L; from about 7.0 g/L to about 25.0 g/L; from about 7.0 g/L to about 15.0 g/L; from about 8.0 g/L to about 12.0 g/L; any of about 2.8 or 3.0 or 3.2 or 3.4 or 3.6 or 3.8 or 4.0 or 4.2 or 4.4 or 4.6 or 4.8 or 5.0 or 5.2 or 5.4 or 5.6 or 6 or 6.2 or 7 or 7.4 or 7.8 or 8 or 9 or 10 or 11 or 12 or 13 or 14 or 15 or 20 or 25 or 30 or 35 or 40 or 45 or 50 g/L; any of 2.8 g/L, 3.0 g/L, 3.2 g/L, 3.4 g/L, 3.6 g/L, 3.8 g/L, 4.0 g/L, 4.2 g/L, 4.4 g/L, 4.6 g/L, 4.8 g/L, 5.0 g/L or 6 g/L, 6.2 g/L, 7 g/L, 8 g/L, 9 g/L, 10 g/L, 11 g/L, 12 g/L, 13 g/L, or 14 g/L; at least any of about 2.8 or 3.2 or 3.4 or 3.6 or 3.8 or 4.0 or 4.2 or 4.6 or 5.0 or 5.6 or 6.2 or 7 or 8 or 9 g/L and no more than about 14 or 13 or 12 or 11 g/L. |
| (e) Plant-derived hydrolysate | from about 1.0 g/L to about 10.0 g/L; from about 1.4 g/L to about 6.2 g/L; from about 1.4 g/L to about 6.0 g/L; from about 1.4 g/L to about 5.5 g/L; from about 1.4 g/L to about 5.0 g/L; from about 1.4 g/L to about 4.5 g/L; from about 1.4 g/L to about 4.0 g/L; from about 1.4 g/L to about 3.5 g/L; from about 1.4 g/L to about 3.0 g/L; from about 1.4 g/L to about 2.5 g/L; from about 1.4 g/L to about 2.0 g/L; from about 2.0 g/L to about 6.2 g/L; from about 2.5 g/L to about 6.2 g/L; from about 3.0 g/L to about 6.2 g/L; from about 3.5 g/L to about 6.2 g/L; from about 4.0 g/L to about 6.2 g/L; from about 4.5 g/L to about 6.2 g/L; from about 5.0 g/L to about 6.2 g/L; from about 5.5 g/L to about 6.2 g/L; from about 1.5 g/L to about 6.0 g/L; from about 2.0 g/L to about 5.5 g/L; from about 2.5 g/L to about 5.0 g/L; from about 3.0 g/L to about 4.5 g/L; from about 3.0 g/L to about 3.2 g/L; from about 3.5 g/L to about 4.0 g/L; from about 1.4 g/L to about 3.4 g/L; from about 1.5 g/L to about 3.0 g/L; from about 1.75 g/L to about 2.8 g/L; from about 1.5 g/L to about 5.5 g/L; from about 1.5 g/L to about 4.5 g/L; from about 1.5 g/L to about 3.5 g/L; from about 1.5 g/L to about 2.5 g/L from about 1.75 g/L to about 2.75 g/L; from about 2.0 g/L to about 3.0 g/L; from about 2.25 g/L to about 2.75 g/L; any of about 1.4 or 1.5 or 1.75 or 2.0 or 2.25 or 2.5 or 2.8 or 3.0 or 3.1 or 3.25 or 3.4 or 3.5 or 3.75 or 4.0 g/L; any of 1.4 g/L, 1.5 g/L, 1.75 g/L, 2.0 g/L, 2.25 g/L, 2.5 g/L, 2.8 g/L, 3.0 g/L, 3.2 g/L, 3.25 g/L, 3.4, 3.75, or 4.0 g/L; at least any of about 1.4 or 1.5 or 1.75 g/L and no more than about 3.4 or 3 or 2.8 g/L. |

In one variation, insulin is present in the cell culture media at a concentration of from about 1.0 mg/L to about 100.0 mg/L or from about 5.0 mg/L to about 80.0 mg/L or from about 5.0 mg/L to about 60.0 mg/L or from about 5.0 mg/L to about 50.0 mg/L or from about 5.0 mg/L to about 40.0 mg/L or from about 5.0 mg/L to about 30.0 mg/L or from about 5.0 mg/L to about 25.0 mg/L or from about 10.0 mg/L to about 25.0 mg/L or from about 10.0 mg/L to about 30.0 mg/L or from about 15.0 mg/L to about 20.0 mg/L or from about 5.0 mg/L to about 15.0 mg/L or from about 6.0 mg/L to about 12.0 mg/L or from about 7.0 mg/L to about 11.0 mg/L or from about 8.0 mg/L to about 10.0 mg/L or at a concentration of about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L or at a concentration of about any one of 7 mg/L, 8.0 mg/L, 9.0 mg/L, 10.0 mg/L or 11.0 mg/L.

In one variation, copper is present in the cell culture media at a concentration of from about 69.0 nM to about 400.0 nM or from about 80 nM to about 400 nM or from about 100 nM to about 400 nM or from about 125 nM to about 400 nM or from about 150 nM to about 400 nM or from about 200 nM to about 400 nM or from about 250 nM to about 400 nM or from about 300 nM to about 400 nM or from about 325 nM to about 375 nM or from about 325 nM to about 350 nM or at a concentration of about any one of 100 nM, 125 nM, 150 nM, 175 nM, 200 nM, 225 nM, 250 nM, 275 nM, 300 nM, 325 nM, 350 nM, 375 nM or 400 nM or at a concentration of about any one of 330 nM, 335 nM, 340 nM, 345 nM or 350 nM or at a concentration of about 335 nM, 336 nM, 337 nM, 338 nM, 339 nM or 400 nM or at a concentration of about 339 nM.

In one variation cystine is present in the cell culture medium at a concentration of from about 0.8 mM to about 2.5 mM or from about 0.8 mM to about 2.0 mM or from about 0.8 mM to about 1.75 mM or from about 0.8 mM to about 1.5 mM or from about 1.0 mM to about 2.0 mM or from about 1.0 mM to about 1.5 mM or from about 1.2 mM to about 1.4 mM or at a concentration of about any one of 0.8 mM or 0.9 mM or 1.0 mM or 1.1 mM or 1.2 mM or 1.3 mM or 1.4 mM or 1.5 mM or at a concentration of about any one of 1.1 mM, 1.3 mM or 1.5 mM or at a concentration of about 1.3 mM.

In one variation, an animal-derived hydrolysate is present in the cell culture media at a concentration of from about 5.6 g/L to about 38.0 g/L or from about 7.0 g/L to about 35.0 g/L or from about 7.0 g/L to about 25.0 g/L or from about 7.0 g/L to about 15.0 g/L or from about 8.0 g/L to about 12.0 g/L or from about 7.0 g/L to about 11.0 g/L or about any one of 5 g/L, 10 g/L, 15 g/L, 20 g/L, 25 g/L, 30 g/L, 35 g/L, 40 g/L, 45 g/L or 50 g/L or about any one of 5 g/L, 6 g/L, 7 g/L, 8 g/L, 9 g/L, 10 g/L, 11 g/L, or 12 g/L or about 10 g/L.

In one variation, an plant-derived hydrolysate is present in the cell culture media at a concentration of from about 1.4 g/L to about 6.2 g/L or from about 1.5 g/L to about 5.5 g/L or from about 1.5 g/L to about 4.5 g/L or from about 1.5 g/L to about 3.5 g/L or from about 1.5 g/L to about 2.5 g/L or from about 1.75 g/L to about 2.75 g/L or from about 2.0 g/L to about 3.0 g/L or from about 2.25 g/L to about 2.75 g/L or about any one of 1.75 g/L, 2.0 g/L, 2.25 g/L, 2.5 g/L, 3.0 g/L, 3.25, 3.5 g/L, 3.75 g/L, or 4.0 g/L or about any one of 2.0 g/L, 2.25 g/L, 2.5 g/L or 3.0 g/L or about 2.5 g/L.

In a further variation, cysteine is present in the cell culture medium. Cysteine may in one aspect be added to a basal cell culture medium (e.g., by supplementing the basal cell culture medium with a feed medium comprising cysteine). In one variation, a cell culture medium comprises cysteine (which may be added to a basal cell culture medium that does not comprise cysteine via a feed medium comprising cysteine) in a concentration of from about 0.5 mM to about 5.0 mM or from about 1.0 mM to about 12.0 mM or from about 2.0 mM to about 10.0 mM or from about 2.0 mM to about 8.0 mM or about 1.0 mM to about 10.0 mM or from about 1.0 mM to about 8.0 mM or from about 2.0 mM to about 12.0 mM or from about 3.0 mM to about 12.0 mM or from about 4.0 mM to about 12.0 mM or from about 5.0 mM to about 12.0 mM or from about 6.0 mM to about 12.0 mM or from about 6.0 mM to about 10.0 mM or from about 6.0 mM to about 8.0 mM or about any one of 0.5 mM, 0.8 mM, 1.0 mM, 1.5 mM, 2.0 mM, 2.5 mM, 5.0 mM, 5.5 mM, 6.0 mM, 6.5 mM, 7.0 mM, 7.5 mM, 8.0 mM, 8.5 mM or 9.0 mM. In one aspect, cysteine is added to a basal cell culture media (which addition may be at any point in time of the cell culture cycle and may be in one or more amounts, which may be the same or different), in an amount such that cysteine is present in the cell culture media at a concentration of about 7.5 mM.

In a further variation, cystine is present in the cell culture medium. Cystine may in one aspect be added to a basal cell culture medium (e.g., by supplementing the basal cell culture medium which may or may not already comprise cystine with a feed medium comprising cystine). In one variation, a cell culture medium comprises cystine (which may be added to a basal cell culture medium via a feed medium comprising cystine) in a concentration of from about 0.5 mM to about 5.0 mM, such as in an amount to provide about 0.8 mM cysteine in the cell culture medium.

In certain embodiments, the cell culture medium comprises cystine but is free of cysteine.

The cell culture medium (e.g., a basal cell culture medium) may further be supplemented with an additional cell culture medium components (e.g., such as via a feed cell culture medium). In one aspect, the additional cell culture medium component comprises insulin. In another aspect, the additional cell culture medium component comprises insulin and cysteine. A cell culture media provided herein may be supplemented with any amount of insulin and/or cysteine that is suitable for culturing a cell. In one aspect, insulin is added to a cell culture medium (e.g., added to a basal cell culture medium at one or more point in time of the cell culture cycle) in an amount to provide a concentration of insulin in the cell culture of about 15 mg/L or about 25 mg/L. In one aspect, insulin is added to a cell culture medium (e.g., added to a basal cell culture medium at one or more point in time of the cell culture cycle) in an amount to provide a concentration of insulin in the cell culture selected from the group consisting of: from about 1.0 mg/L to about 100.0 mg/L; from about 10.0 mg/L to about 100.0 mg/L; from about 10.0 mg/L to about 50.0 mg/L; from about 10.0 mg/L to about 35.0 mg/L; from about 10.0 mg/L to about 25.0 mg/L; from about 5.0 mg/L to about 80.0 mg/L; from about 5.0 mg/L to about 60.0 mg/L; from about 5.0 mg/L to about 50.0 mg/L; from about 5.0 mg/L to about 30.0 mg/L; from about 5.0 mg/L to about 25.0 mg/L; from about 10.0 mg/L to about 25.0 mg/L; from about 10.0 mg/L to about 30.0 mg/L; from about 15.0 mg/L to about 20.0 mg/L; from about 5.0 mg/L to about 15.0 mg/L; from about 6.0 mg/L to about 12.0 mg/L; from about 7.0 mg/L to about 11.0 mg/L; from about 8.0 mg/L to about 10.0 mg/L; about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L; about any one of 7 mg/L, 8.0 mg/L, 9.0 mg/L, 10.0 mg/L and 11.0 mg/L. In another aspect, cysteine is added to a cell culture medium (e.g., added to a basal cell culture medium at one or more point in time of the cell culture cycle) in an amount to provide a concentration of cysteine in the cell culture selected from the group consisting of: from about 1.0 mM to about 12.0 mM or from about 2.0 mM to about 10.0 mM or from about 2.0 mM to about 8.0 mM or about 1.0 mM to about 10.0 mM or from about 1.0 mM to about 8.0 mM or from about 2.0 mM to about 12.0 mM or from about 3.0 mM to about 12.0 mM or from about 4.0 mM to about 12.0 mM or from about 5.0 mM to about 12.0 mM or from about 6.0 mM to about 12.0 mM or from about 6.0 mM to about 10.0 mM or from about 6.0 mM to about 8.0 mM or about any one of 5.0 mM, 5.5 mM, 6.0 mM, 6.5 mM, 7.0 mM, 7.5 mM, 8.0 mM, 8.5 mM or 9.0 mM. In another aspect, cystine is added to a cell culture medium (e.g., added to a basal cell culture medium at one or more point in time of the cell culture cycle) in an amount to provide a concentration of cystine in the cell culture of from about 0.1 mM to about 1.5 mM, such as a concentration of about 0.2 mM.

In some aspects, a cell culture medium provided herein comprises from about 5.0 mg/L to about 14.0 mg/L, from about 5.5 mg/L to about 13.0 mg/L, from about 6.0 mg/L to about 12.0 mg/L, from about 7.0 mg/L to about 11.0 mg/L, from about 8.0 mg/L to about 10.0 mg/L, or from about 8.5 mg/L to about 14.0 mg/L insulin. It is understood that the cell culture medium comprising insulin may further comprise any one or more of copper and cystine in any amount provided herein. For example, it is understood that a cell culture medium comprising from about 6.0 mg/L to about 12.0 mg/L insulin may further comprise from about 70 nM to about 400 nM of copper and/or from about 0.5 mM to about 2.5 mM cystine and may further comprise an animal-derived hydrolysate and/or plant-derived hydrolysate, for example an animal-derived hydrolysate from about 5.5 g/L to about 40.0 g/L and/or a plant-derived hydrolysate from about 1.5 g/L to about 6.5 g/L.

In other aspects, a cell culture medium provided herein comprises from about 65 nM to about 400 nM, from about 70 nM to about 375 nM, from about 75 nM to about 350 nM, from about 80 nM to about 325 nM, from about 85 nM to about 300 nM, or from about 90 nM to about 275 nM copper. It is understood that the cell culture medium comprising copper may further comprise any one or more of insulin and cystine in any amount provided herein. For example, it is understood that a cell culture medium comprising from about 85 nM to about 300 nM copper may further comprise from about 0.8 mM to about 1.75 mM of cystine and/or from about 8.0 mg/L to about 12.0 mg/L insulin and may further comprise an animal-derived hydrolysate and/or plant-derived hydrolysate, for example an animal-derived hydrolysate from about 5.5 g/L to about 40.0 g/L and/or a plant-derived hydrolysate from about 1.5 g/L to about 6.5 g/L.

In some aspects, a cell culture medium provided herein comprises from about 0.8 mM to about 1.75 mM, from about 0.9 mM to about 1.50 mM, from about 1.0 mM to about 1.40 mM, or from about 1.0 mM to about 1.30 mM cystine. It is understood that the cell culture medium comprising cystine may further comprise any one or more of insulin and copper in any amount provided herein. For example, it is understood that a cell culture medium comprising from about 0.8 mM to about 1.75 mM cystine may further comprise from about 70 nM to about 375 nM of copper and/or from about 8.0 mg/L to about 12.0 mg/L insulin and may further comprise an animal-derived hydrolysate and/or plant-derived hydrolysate, for example an animal-derived hydrolysate from about 5.5 g/L to about 40.0 g/L and/or a plant-derived hydrolysate from about 1.5 g/L to about 6.5 g/L.

In some embodiments, the cell culture medium further comprises an animal-derived hydrolysate in amounts as described in Table 1. In other embodiments, the cell culture medium further comprises a plant-derived hydrolysate in amounts as described in Table 1. In some embodiments, the cell culture medium further comprises both an animal-derived hydrolysate and a plant-derived hydrolysate in amounts as described in Table 1.

In some aspects, a cell culture medium provided herein comprises from about 1.5 g/L to about 6.0 g/L, from about 2.0 g/L to about 5.5 g/L, from about 2.5 g/L to about 5.0 g/L, from about 3.0 g/L to about 4.5 g/L, or from about 3.5 g/L to about 4.0 g/L plant-derived hydrolysate. It is understood that the cell culture medium comprising plant-derived hydrolysate may further comprise any one or more of cystine, insulin and copper in any amount provided herein. For example, it is understood that a cell culture medium comprising from about 0.8 mM to about 1.75 mM cystine may further comprise from about 70 nM to about 375 nM of copper and/or from about 8.0 mg/L to about 12.0 mg/L insulin and may further comprise an animal-derived hydrolysate, for example an animal-derived hydrolysate from about 6.0 g/L to about 20.0 g/L.

In some aspects, a cell culture medium provided herein comprises from about 6.0 g/L to about 35.0 g/L, from about 7.0 g/L to about 30.0 g/L, from about 8.0 g/L to about 25.0 g/L, from about 9.0 g/L to about 20 g/L, or from about 10.0 g/L to about 15.0 g/L animal-derived hydrolysate. It is understood that the cell culture medium comprising animal-derived hydrolysate may further comprise any one or more of cystine, insulin and copper in any amount provided herein. For example, it is understood that a cell culture medium comprising from about 0.8 mM to about 1.75 mM cystine may further comprise from about 70 nM to about 375 nM of copper and/or from about 8.0 mg/L to about 12.0 mg/L insulin and may further comprise an plant-derived hydrolysate, for example an plant-derived hydrolysate from about 1.5 g/L to about 3.0 g/L.

In some of the embodiments herein, the cell culture medium comprises from about 0.9 mM to about 1.5 mM cystine. In some of the embodiments herein, the cell culture medium comprises from about 1.4 mg/L to about 11.0 mg/L insulin or from about 1.44 mg/L to about 66.0 mg/L insulin. In some of the embodiments herein, the cell culture medium comprises from about 26.0 nM to about 400.0 nM copper. In some aspects, a cell culture medium comprises two or more components selected from: (a) about 69.0 nM to about 400.0 nM copper, (b) from about 7.0 mg/L to about 11.0 mg/L insulin or from about 1.44 mg/L to about 66 mg/L insulin, and (c) from about 0.8 mM to about 2.5 mM cystine.

Cell culture media components described herein (e.g., a cell culture media comprising any one or more of copper, insulin, cystine, an animal-derived hydrolysate and a plant-derived hydrolysate) may be added to a cell culture medium in a form that is known in the art, such as a salt, a hydrate or combination thereof. The cell culture media components can also be provided to the cell culture media as a solution, an extract, or in solid form. As a non-limiting example, cystine may be provided to the cell culture medium as the disodium salt monohydrate powder. Protein hydrolysates, also known as peptones, are typically manufactured by enzymatic digestion of a variety of biologically based starting materials such as animal tissues, milk-derived products, microorganisms or plants. The hydrolysate used in the cell culture medium provided herein can be derived from a plant or an animal (e.g., plant-derived hydrolysate and/or animal-derived hydrolysate). A plant hydrolysate as described herein can be derived from, but not limited to, wheat gluten, maize, cereal, soy, or cottonseed. An animal hydrolysate as described herein can be derived from, but not limited to, bovine, chicken, caprine, equine, human, ovine, porcine, or rabbit or other animals.

A method of preparing a cell culture medium for use in culturing a mammalian cell comprising a nucleic acid encoding bevacizumab, or a fragment thereof, is also provided, wherein the method comprises combining any two or more of copper, insulin and cystine in a composition suitable for cell culture. In one aspect, the method comprises adding any two or more of copper, insulin and cystine to a composition suitable for cell culture, wherein the two or more of copper, insulin and cystine may be added to the composition sequentially or simultaneously. In a further variation, a method of preparing a cell culture medium for use in culturing a mammalian cell comprising a nucleic acid encoding bevacizumab, or a fragment thereof, is provided, wherein the method comprises combining any two or more of copper, insulin and cystine in a composition suitable for cell culture at a first period of time and wherein the method further comprises adding an amount of insulin at a second period of time, such as at least once, at least twice, at least three times, at least four time, at least five times, at least six times, at least seven times, etc. of a cell growth cycle. In some embodiments, a cell growth cycle is at least 1 day, 2 days, 3 days, 4 days, 5 days, 6 days, 7 days, 8 days, 9 days, 10 days, 11 days, 12 days, 13 days, 14 days, 15 days, 16 days, 17 days, 18, days, 19 days, 20 days, or any amount of days wherein the cells may remain in cell culture while still remaining viable. In one variation of a method of preparing a cell culture medium, cystine is added in an amount to provide about 0.9 mM to about 1.5 mM cystine in the cell culture medium. In another variation of a method of preparing a cell culture medium, insulin is added in an amount to provide from about 1.4 mg/L to about 11.0 mg/L insulin or from about 1.44 mg/L to about 66.0 mg/L insulin in the cell culture medium. In another variation of a method of preparing a cell culture medium, copper is added in an amount to provide from about 26.0 nM to about 400.0 nM copper in the cell culture medium. In some aspects, a cell culture medium is prepared by combining two or more components selected from: (a) copper in an amount to provide about 69.0 nM to about 400.0 nM copper in the cell culture medium, (b) insulin in an amount to provide from about 7.0 mg/L to about 11.0 mg/L or from about 1.44 mg/L to about 66 mg/L insulin in the cell culture medium, and (c) cystine in an amount to provide from about 0.8 mM to about 2.5 mM cystine in the cell culture medium.

In some embodiments herein, the cell culture medium is a basal cell culture medium. In other embodiments herein, the cell culture medium is a feed cell culture medium. In some embodiments herein, the cell culture medium is a basal cell culture medium comprising at least one of copper, insulin, and cystine, and where the basal cell culture medium is supplemented (e.g., at a period of time following initiation of a cell culture cycle, such as any one of at least two times, at least three times, at least four times, at least five times, at least six times, at least seven times, etc. of a cell culture cycle) with a feed cell culture medium comprising any one or more of insulin, an animal-derived hydrolysate and a plant-derived hydrolysate.

Individual media components provided herein may be present in amounts that result in one or more advantageous properties for culturing cells comprising a nucleic acid encoding bevacizumab, or a fragment thereof, and/or for bevacizumab production from cell culture. Advantageous properties include, but are not limited to, increased cell viability, increase in the amount of bevacizumab produced from the cell (e.g., enhanced bevacizumab titer) and/or reduced oxidation of bevacizumab in cell culture. Advantageous properties of the cell culture media provided herein may also include maintaining or enhancing the amount of bevacizumab produced by the cells (e.g., antibody titer) while maintaining the N-glycosylation profile, the charge heterogeneity and/or the amino acid sequence integrity of bevacizumab, or a fragment thereof. These advantageous properties are applicable to methods of culturing a cell comprising a nucleic acid encoding bevacizumab, or a fragment thereof and to methods of producing bevacizumab, or a fragment thereof in cell culture as described herein.

A cell culture medium provided herein in one aspect results in one or more favorable product quality attribute or advantageous property when used in a method of producing bevacizumab, or a fragment thereof. In one variation, use of the cell culture medium provided herein increases the amount of bevacizumab produced by the cells (e.g., enhances antibody titer) as compared to the amount of bevacizumab, or a fragment thereof, produced by culturing the cell producing bevacizumab in a different cell culture medium.

As would be understood by the skilled artisan, the cell culture media detailed herein may comprise other components (e.g., besides the one or more of copper, insulin, and cystine, and optionally peptone hydrolysate) that are useful for cell culture. For example, it is understood that the cell culture media may comprise additional components such as amino acids (e.g., glutamine, arginine, or asparagine), vitamins (including but not limited to B vitamins such as any one or more of vitamin B1, vitamin B2, vitamin B3, vitamin B6, vitamin B7, vitamin B9, or vitamin B 12), trace elements, transition metals (including but not limited to nickel, iron (e.g., ferric iron or ferrous iron), or zinc), and other media components. Any media provided herein may also be supplemented with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements and glucose or an equivalent energy source. Additional cell culture media components, such as those listed herein, may be included in the cell culture medium at appropriate concentrations that would be known to those skilled in the art.

III. Methods and Uses of the Invention

Provided herein are methods of culturing cells used in the production bevacizumab, or a fragment thereof, and use of cell culture media that comprise one or more of copper, insulin and cystine. In some aspects, a method is provided for culturing a mammalian cell comprising a nucleic acid encoding bevacizumab or fragment thereof, wherein the method comprises the step of contacting the mammalian cell with a cell culture medium comprising at least two of copper, insulin and cystine, wherein the cell culture medium may additionally comprise a plant-derived hydrolysate, an animal-plant-derived hydrolysate or both a plant-derived hydrolysate and an animal-derived hydrolysate. In some embodiments, the cell culture media comprises insulin. In some of the embodiments herein, the cell culture media comprises copper. In some of the embodiments herein, the cell culture media comprises cystine. In some of the embodiments herein, the cell culture media comprises copper and cystine. In some of the embodiments herein, the cell culture media comprises copper and insulin. In some of the embodiments herein, the cell culture media comprises insulin and cystine. In some of the embodiments herein, the amount of the components in the cell culture medium (e.g., the amount of copper, insulin, cystine, plant-derived hydrolysate and/or animal-derived hydrolysate) is in an amount selected from a value provided in Table 1. In some embodiments, the method further comprises the step of adding an additional amount of insulin to the medium. The additional amount of insulin can be added to the cell culture medium at least once, at least three times, at least 6 times or at least 12 times during the cell culture cycle. In some of the embodiments herein, the additional amount of insulin added to the cell culture is added in an amount to provide insulin in the cell culture medium at a concentration selected from Table 1 such as from about 1 mg/L to about 44 mg/L. In some aspects, the cell culture medium further comprises an animal-derived hydrolysate, a plant-derived hydrolysate, or both an animal-derived hydrolysate and a plant-derived hydrolysate.

In some other aspects, a method is provided for culturing a cell comprising a nucleic acid encoding bevacizumab or fragment thereof, wherein the method comprises the step of contacting the cell with a cell culture medium comprising two or more components selected from the group consisting of copper, insulin, and cystine. In some embodiments herein, the cell culture medium comprises insulin at a concentration of from about 7.0 mg/L to about 11.0 mg/L. In some embodiments herein, the cell culture medium comprises copper at a concentration of from about 69.0 nM to about 400.0 nM. In some embodiments herein, the cell culture medium comprises cystine at a concentration of from about 0.8 mM to about 2.5 mM. In some embodiments herein the cell culture medium comprises insulin at a concentration of from about 7.0 mg/L to about 11.0 mg/L and copper at a concentration of from about 69.0 nM to about 400.0 nM. In some embodiments herein the cell culture medium comprises insulin at a concentration of from about 7.0 mg/L to about 11.0 mg/L and cystine at a concentration of from about 0.8 mM to about 2.5 mM. In some embodiments herein the cell culture medium comprises copper at a concentration of from about 69.0 nM to about 400.0 nM and cystine at a concentration of from about 0.8 mM to about 2.5 mM. In some embodiments herein the cell culture medium comprises insulin at a concentration of from about 7.0 mg/L to about 11.0 mg/L, copper at a concentration of from about 69.0 nM to about 400.0 nM and cystine at a concentration of from about 0.8 mM to about 2.5 mM. In any of the embodiments herein, the cell culture medium may comprise cystine, insulin and/or copper in an amount selected from Table 1. In some of the embodiments herein, the method further comprises the step of adding an additional amount of insulin to the cell culture medium provided herein (e.g., such as via a feed medium introduced to the basal cell culture medium at a period of time following initiation of the cell culture cycle). The additional amount of insulin can be added to the cell culture medium at least once, at least two times, at three times, at least six times, at least nine times, at least twelve times, or at least fourteen times during the cell culture cycle. In some of the embodiments herein, the additional amount of insulin added to the cell culture is added in an amount to provide insulin in the cell culture medium at a concentration selected from Table 1 such as 5.6 mg/L to about 66 mg/L. In some aspects, the cell culture medium further comprises an animal-derived hydrolysate, a plant-derived hydrolysate, or both an animal-derived hydrolysate and a plant-derived hydrolysate. In some of the embodiments herein, the method further comprises the step of adding an additional amount of animal-derived hydrolysate and plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and plant-derived hydrolysate added to the cell culture is added in an amount to provide animal-derived hydrolysate and plant-derived hydrolysate in the cell culture medium at a concentration selected from the concentrations listed in Table 1.

In another aspect, provided herein are methods of producing bevacizumab or a fragment thereof, wherein the method comprises the step of contacting a cell capable of producing bevacizumab or a fragment thereof with a cell culture medium comprising two or more components selected from the group consisting of copper, insulin, and cystine. In some embodiments herein, the cell culture medium comprises insulin at a concentration of from about 7.0 mg/L to about 11.0 mg/L. In some embodiments herein, the cell culture medium comprises copper at a concentration of from about 69.0 nM to about 400.0 nM. In some embodiments herein, the cell culture medium comprises cystine at a concentration of from about 0.8 mM to about 2.5 mM. In any of the embodiments herein, the cell culture medium may comprise cystine, insulin or copper in an amount selected from Table 1. In some of the embodiments herein, the method further comprises the step of adding an additional amount of insulin to the cull culture medium provided herein. Insulin may be added to the cell culture medium in any amount that is suitable for cell culture. In one aspect, insulin is added to the cell culture medium in an amount to provide insulin in the cell culture medium at a concentration selected from the concentrations listed in Table 1. In a particular aspect, insulin is added to the cell culture medium in an amount to provide insulin in the cell culture medium at a concentration selected from the group consisting of: from about 1.0 mg/L to about 100.0 mg/L; from about 5.0 mg/L to about 80.0 mg/L; from about 5.0 mg/L to about 60.0 mg/L; from about 5.0 mg/L to about 50.0 mg/L; from about 5.0 mg/L to about 40.0 mg/L; from about 5.0 mg/L to about 30.0 mg/L; from about 5.0 mg/L to about 25.0 mg/L; from about 10.0 mg/L to about 25.0 mg/L; from about 10.0 mg/L to about 30.0 mg/L; from about 15.0 mg/L to about 20.0 mg/L; from about 5.0 mg/L to about 15.0 mg/L; from about 6.0 mg/L to about 12.0 mg/L; from about 7.0 mg/L to about 11.0 mg/L and from about 8.0 mg/L to about 10.0 mg/L. In another aspect, insulin is added to the cell culture medium in an amount to provide insulin in the cell culture medium at a concentration of about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L. In a further aspect, insulin is added to the cell culture medium in an amount to provide insulin in the cell culture medium at a concentration of about any one of 7 mg/L, 8.0 mg/L, 9.0 mg/L, 10.0 mg/L or 11.0 mg/L. The additional amount of insulin can be added to the cell culture medium at any time during the cell culture cycle. For example, insulin may be added at any one or more of days 1-20 for a 20 day cell culture cycle (e.g., at any one or more of days 1, 2, 3, 4, 5, 6, 7, 8, 9, 10, 11, 12, 13, 14, 15, 16, 17, 18, 19 or 20). When an additional amount of insulin is added, it may be added in any amount, which amount may be the same or different when insulin is added more than once during a cell culture cycle. It is therefore appreciated that for a 14 day cell culture cycle, insulin may be added at any one or more of days 1-14 (e.g., at any one or more of days 1, 2, 3, 4, 5, 6, 7, 8, 9, 10, 11, 12, 13 or 14) in any amount, which amount may be the same or different when insulin is added more than one during a cell culture cycle. The additional amount of insulin can be added to the cell culture medium at least once, at least two times, at three times, at least six times, at least nine times, at least twelve times, or at least fourteen times during the cell culture cycle. In some of the embodiments herein, the additional amount of insulin added to the cell culture is added in an amount to provide insulin in the cell culture medium at a concentration selected from Table 1 such as 5.6 mg/L to about 66 mg/L. In some aspects, the cell culture medium further comprises an animal-derived hydrolysate, a plant-derived hydrolysate, or both an animal-derived hydrolysate and a plant-derived hydrolysate. In some of the embodiments herein, the method further comprises the step of adding an additional amount of animal-derived hydrolysate and plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and plant-derived hydrolysate added to the cell culture is added in an amount to provide animal-derived hydrolysate and plant-derived hydrolysate in the cell culture medium at a concentration selected from the concentrations listed in Table 1.

In some of the embodiments herein, the method increases the amount of bevacizumab or fragment thereof produced by the mammalian cell as compared to a the amount of bevacizumab or fragment thereof the mammalian cell produces when cultured in a cell culture medium that does not comprise one or more of components listed in Table 1. In some embodiments, the amount of bevacizumab or fragment thereof produced by a cell cultured in a cell culture medium comprising at least two of copper, insulin and cystine is increased by at least 5%, 6,%, 7%, 8%, 9%, 10%, 11%, 12%, 13%, 14%, 15%, 16%, 18%, 19%, 20%, 25%, 30%, 35%, 40%, 45%, or 50% as compared to the amount of bevacizumab or fragment thereof produced by the cell when cultured in a cell culture medium that does not comprise at least two of copper, insulin and cystine.

The cell culture medium provided herein can be used a basal cell culture medium and/or as a feed cell culture medium. In some embodiments, a cell culture medium provided herein is used in a method for culturing the cell during the cell's growth phase. In some embodiments, a cell culture medium provided herein is used in a method for culturing the cell during the cell's production phase.

It is understood that any of the methods detailed herein including: (i) a method of producing bevacizumab, or a fragment thereof; (ii) a method of culturing a mammalian cell comprising a nucleic acid encoding bevacizumab, or a fragment thereof; and (iii) a method of enhancing production of bevacizumab, or a fragment thereof, (e.g., enhancing titer yields of bevacizumab, or a fragment thereof) from a mammalian cell comprising a nucleic acid encoding bevacizumab, or a fragment thereof, may be carried out in any suitable scale (e.g., any scale that produces bevacizumab, or a fragment thereof). In one aspect, any of the methods detailed herein are performed on a scale that is commensurate in scope with commercial production of bevacizumab, or a fragment thereof. For example, in one variation, a cell capable of producing bevacizumab may be cultured in a cell culture medium provided herein wherein the culturing occurs in a culturing vessel that is capable of holding a commercial batch of bevacizumab, such as in a culturing vessel capable of holding at least 10,000 L of cell culture (e.g., the methods in one aspect are carried out on at least a 10,000 L cell culture scale, such as a 12,000 L cell culture scale).

In further embodiments of the methods provided herein, the bevacizumab or a fragment thereof is recovered from the cell culture. A composition comprising the recovered bevacizumab or a fragment thereof can be subjected to at least one purification step before assessment of, e.g., a quality attribute. In a further embodiment, the composition is a pharmaceutical composition comprising bevacizumab or a fragment thereof and a pharmaceutically acceptable carrier.

Other methods and cell culture media are provided throughout, such as in the Brief Summary of the Invention and elsewhere.

Polypeptide Production

The cell culture media detailed herein can be used in a method of culturing cells to produce bevacizumab or a fragment thereof. The medium may be used in a method of culturing cells capable of producing bevacizumab or a fragment thereof, whether by batch culture, fed batch culture or perfusion culture. In one embodiment, bevacizumab or a fragment thereof is directly secreted into the medium by the host cell. In another embodiment, bevacizumab or a fragment thereof is released into the medium by lysis of a cell comprising a nucleic acid encoding the antibody or fragment thereof.

Bevacizumab or a fragment thereof that is expressible in a host cell may be produced in accordance with the present disclosure and may be present in the compositions provided.

Methods for producing antibodies and fragments thereof, in cell culture are well known in the art. Provided herein are non-limiting exemplary methods for producing an antibody (e.g., full length antibodies, antibody fragments and multispecific antibodies) in cell culture. See *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); *Short Protocols in Molecular Biology* (Ausubel et al., eds., J. Wiley and Sons, 2002); *Current Protocols in Protein Science*, (Horswill et al., 2006); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010) for generally well understood and commonly employed techniques and procedures for the production of antibodies (e.g., bevacizumab), which are all incorporated herein by reference in their entirety.

Cell Culture and Antibody Production

Generally the cells are combined (contacted) with any of the cell culture media described herein under one or more conditions that promote any of cell growth, maintenance and/or antibody production. Methods of culturing a cell and producing an antibody employ a culturing vessel (bioreactor) to contain the cell and cell culture medium. The culturing vessel can be composed of any material that is suitable for culturing cells, including glass, plastic or metal. Typically, the culturing vessel will be at least 1 liter and may be 10, 100, 250, 500, 1000, 2500, 5000, 8000, 10,000 liters or more (e.g., a 12,000 liter vessel). In one aspect the culturing vessel is capable of containing at least 2 liters, at least 10 liters, at least 100 liters, at least 500 liters, at least 1,000 liters, at least 2,500 liters, at least 5,000 liters, at least 7,500 liters, at least 10,000 liters, at least 12,000 liters or more of a cell culture medium provided herein as is required for producing manufacturing scale amounts of bevacizumab from cell culture. Thus, the compositions and methods provided herein may find use in a manufacturing-scale production of bevacizumab, or a fragment thereof. The culture conditions, such as temperature, pH, and the like, are those previously used with the host cell selected for expression, and will be apparent to the ordinarily skilled artisan. Culturing conditions that may be adjusted during the culturing process include but are not limited to pH and temperature. In some of the embodiments herein, the pH is at least 7.0, 7.15, 7.2, 7.25, 7.30, 7.35, 7.4, 7.45, or 7.50 but no more than 8.0. The number of cells comprising a nucleic acid encoding bevacizumab, or a fragment thereof, that can be inoculated into a cell culture medium provided herein will be apparent to one of skill in the art. For example, about $1.0 \times 10^6$ to about $2.0 \times 10^6$ cells (including any of about $1.1 \times 10^6$, about $1.2 \times 10^6$ about $1.3 \times 10^6$, about $1.4 \times 10^6$, about $1.5 \times 10^6$, about $1.6 \times 10^6$, about $1.7 \times 10^6$, about $1.8 \times 10^6$ or about $1.9 \times 10^6$) comprising a nucleic acid encoding bevacizumab, or a fragment thereof, can be inoculated in a medium provided herein for initiation of a cell culture cycle. In one aspect, the number of cells comprising a nucleic acid encoding bevacizumab, or a fragment thereof, that can be inoculated into a cell culture medium provided herein is from about $1.2 \times 10^6$ to about $1.8 \times 10^6$ cells or from about $1.3 \times 10^6$ to about $1.7 \times 10^6$ cells or from about $1.5 \times 10^6$ to about $1.7 \times 10^6$ cells.

A cell culture is generally maintained in the initial growth phase under conditions conducive to the survival, growth and viability (maintenance) of the cell culture. The precise conditions will vary depending on the cell type, the organism from which the cell was derived, and the nature and character of the expressed antibody or fragment thereof.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be cultured during the initial growth phase for a greater or lesser amount of time. In one variation, the cells are cultured for a period of time sufficient to achieve a viable cell density that is a given percentage of the maximal viable cell density that the cells would eventually reach if allowed to grow undisturbed. For example, the cells may be cultured for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are cultured, and the intrinsic growth rate of the cells, the cells may be cultured for 0, 1, 2, 3, 4, 5, 6, 7, 8, 9, 10, 11, 12, 13, 14, 15, 16, 17, 18, 19, or more days. In some cases, the cells may be allowed to grow for a month or more.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

An initial culturing step is a growth phase, wherein batch cell culture conditions are modified to enhance growth of recombinant cells, to produce a seed train. The growth phase generally refers to the period of exponential growth where cells are generally rapidly dividing, e.g. growing. During this phase, cells are cultured for a period of time, usually 1 to 4 days, e.g. 1, 2, 3, or 4 days, and under such conditions that cell growth is optimal. The determination of the growth cycle for the host cell can be determined for the particular host cell by methods known to those skilled in the art.

In the growth phase, a basal culture medium provided herein and cells may be supplied to the culturing vessel in batch. The culture medium in one aspect contains less than about 5% or less than 1% or less than 0.1% serum and other proteins derived from plants or animals (e.g., animal-derived hydrolysates and/or plant-derived hydrolysates). In some embodiments, the basal medium does not comprise an animal-derived or plant-derived hydrolysate. However, serum and animal-derived proteins can be used if desired. At a particular point in their growth, the cells may form an inoculum to inoculate a culture medium at the start of culturing in the production phase. Alternatively, the production phase may be continuous with the growth phase. The cell growth phase is generally followed by a polypeptide production phase (e.g., antibody production phase).

During the polypeptide production phase, the cell culture may be maintained under a second set of culture conditions (as compared to the growth phase) conducive to the survival and viability of the cell culture and appropriate for expression of the desired polypeptide (e.g., bevacizumab or fragment thereof). For example, during the subsequent production phase, CHO cells express recombinant polypeptides well within a range of 25° C. to 35° C. Multiple discrete temperature shifts may be employed to increase cell density or viability or to increase expression of the recombinant polypeptide. In one embodiment, a method of increasing polypeptide production (e.g., increasing production of bevacizumab or fragment thereof) comprises a one or more temperature shift step during the polypeptide production phase. In a further embodiment, a one or more temperature shift step comprises a shift of the temperature from 37° C. to 35° C., from 35° C. to 333° C., or from 33° C. to 31° C. In some embodiments herein, a one or more temperature shift step comprises a shift of temperature from about 37° C.

on day 0 to 35° C. on day 1 to 33° C. on day 8 and to 31° C. on day 10. In some embodiments herein, a one or more temperature shift step comprises a shift of temperature from about 37° C. on day 0 to 35° C. on day 3 to 33° C. on day 8 and to 31° C. on day 10. In some embodiments herein, a one or more temperature shift step comprises a shift of temperature from about 37° C. on day 0 to 34° C. on day 2.5.

The cells may be maintained in the subsequent production phase until a desired cell density or production titer is reached. In one embodiment, the cells are maintained in the subsequent production phase until the titer of the recombinant polypeptide (e.g., bevacizumab or fragment thereof) reaches a maximum. In other embodiments, the culture may be harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture.

In certain cases, it may be beneficial or necessary to supplement the cell culture during the subsequent production phase with nutrients or other medium components that have been depleted or metabolized by the cells. For example, it might be advantageous to supplement the cell culture with nutrients or other medium components observed to have been depleted during monitoring of the cell culture. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. In one aspect, a basal cell culture is supplemented with insulin and/or plant-derived hydrolysate and/or an animal-derived hydrolysate as detailed herein.

In some embodiments herein, the methods of the invention comprise the supplementation of an additional amount of insulin into the cell culture during the cell production phase. For example, an additional 15 mg/L of insulin may be added to the cell culture on day of the production phase of the cell culture cycle. In another example, an additional 5 mg/L of insulin may be added to the cell culture at least three times during the production phase of the cell culture cycle. In still another example, an additional 5 mg/L of insulin may be added to the cell culture at least six times during the production phase of the cell culture cycle. A cell culture cycle may be at least 3 days, 4 days, 5 days, 6 days, 7 days, 8 days, 9 days, 10 days, 11 days, 12 days, 13 days, or 14 days long. In some embodiments, the cell culture cycle is up to 20 days long. In some embodiments, the cell culture is at least 20 days long. In some embodiments, a cell may be cultured for more than one cell culture cycle. In some of the embodiments herein, the method further comprises the step of adding an additional amount of animal-derived hydrolysate and plant-derived hydrolysate to the cell culture medium provided herein (e.g., such as via a feed medium introduced to the basal cell culture medium at a period of time following initiation of the cell culture cycle). In some of the embodiments herein, the additional amount of animal-derived hydrolysate and plant-derived hydrolysate added to the cell culture is added in an amount to provide animal-derived hydrolysate and plant-derived hydrolysate in the cell culture medium at a concentration selected from the concentrations listed in Table 1.

Antibody Purification

Bevacizumab or a fragment thereof preferably is recovered from the culture medium as a secreted polypeptide, although it also may be recovered from host cell lysates when directly expressed without a secretory signal.

The culture medium or lysate may be centrifuged to remove particulate cell debris. Bevacizumab or a fragment thereof thereafter may be purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX® G-75; and protein A SEPHAROSE® columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the antibody or fragment thereof of interest may require modification to account for changes in the character of the antibody or fragment thereof upon expression in recombinant cell culture. An antibody or fragment thereof can be generally purified using chromatographic techniques (e.g., affinity chromatography with a low pH elution step and ion exchange chromatography to remove process impurities). Purified bevacizumab or a fragment thereof may be concentrated to provide a concentrated protein composition, e.g., one with an antibody concentration of at least 100 mg/mL or 125 mg/mL or 150 mg/mL or a concentration of about 100 mg/mL or 125 mg/mL or 150 mg/mL. It is understood that concentrated polypeptide products may be concentrated up to levels that are permissible under the concentration conditions, e.g., up to a concentration at which the polypeptide is no longer soluble in solution. Non-limiting examples of methods for producing and purifying antibodies for drug formulations are described in Kelley, B. MAbs., 2009, 1(5):443-452, which is incorporated herein in its entirety by reference.

IV. Pharmaceutical Formulations

Compositions comprising the cell culture medium provided herein and one or more other component, such as a cell or a desired antibody or fragment thereof (i.e., bevacizumab or fragment thereof), are also provided. A mammalian cell comprising a nucleic acid encoding bevacizumab or fragment thereof can secrete the antibody or fragment thereof into a cell culture medium of the invention during cell culture. Accordingly, compositions of the invention may comprise a mammalian cell that produces bevacizumab or fragment thereof and a cell culture medium provided herein into which the bevacizumab or fragment thereof is secreted. Compositions comprising bevacizumab or fragment thereof and a cell culture medium provided herein are also contemplated. In some aspects of the invention, a composition comprises (a) a mammalian cell comprising a nucleic acid encoding bevacizumab or fragment thereof; and (b) a cell culture medium as provided herein. In some aspects, the composition comprises (a) bevacizumab or fragment thereof; and (b) a cell culture medium as provided herein, wherein the antibody or fragment thereof is secreted into the medium by a mammalian cell comprising an isolated nucleic acid encoding bevacizumab or fragment thereof. In other aspects, the composition comprises: (a) bevacizumab or fragment thereof; and (b) a cell culture medium as provided herein, wherein the bevacizumab or fragment thereof is released into the medium by lysis of a mammalian cell comprising an isolated nucleic acid encoding the bevacizumab or fragment thereof. The mammalian cell of the composition may be any mammalian cell detailed herein (e.g., a CHO cell) and the medium of the composition may be any medium detailed herein, such as a medium comprising one or more compounds as detailed in Table 1.

Compositions (e.g., pharmaceutical formulations) of bevacizumab or a fragment thereof produced by any of the methods described herein are prepared by mixing bevacizumab or fragment thereof having the desired degree of purity with one or more optional pharmaceutically acceptable carriers (*Remington's Pharmaceutical Sciences* 16th edition, Osol, A. Ed. (1980)), which may be in the form of lyophilized formulations or aqueous solutions. Pharmaceutically acceptable carriers are generally nontoxic to recipients at the dosages and concentrations employed, and include, but are not limited to: buffers, antioxidants, preservatives, low molecular weight (less than about 10 residues) polypeptides, proteins; hydrophilic polymers; amino acids; monosaccharides, disaccharides, and other carbohydrates, chelating agents, sugars, salt-forming counterions, metal complexes (e.g. Zn-protein complexes), and/or non-ionic surfactants. In some embodiments, the pharmaceutical formulation is administered to a mammal such as a human. Pharmaceutical formulations of bevacizumab or fragment thereof can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Accordingly, antibody-containing formulations as provided herein may be suitable for injection, such as subcutaneous injection into an individual (e.g., subcutaneous injection into a human). The pharmaceutical formulations to be used for in vivo administration are generally sterile. Sterility may be readily accomplished, for example by filtration through sterile filtration membranes.

In some aspects, a composition (e.g., pharmaceutical formulation) as provided herein comprises bevacizumab or fragment thereof at a concentration of at least 100 mg/mL, 125 mg/mL, 150 mg/mL, 200 mg/mL, or 250 mg/mL, or at a concentration of about 100 mg/mL, about 125 mg/mL, about 150 mg/mL, about 175 mg/mL, or about 200 mg/mL. In other aspects, a composition (e.g., pharmaceutical formulation) as provided herein comprises bevacizumab or fragment thereof at a concentration of at least 1 mg/mL, 10 mg/mL, 25 mg/mL, 50 mg/mL, or 75 mg/mL, or at a concentration of about 1 mg/mL, about 10 mg/mL, about 25 mg/mL, about 50 mg/mL, or about 75 mg/mL.

V. Articles of Manufacture and Kits

A kit for supplementing a cell culture medium with at least two of copper, insulin and cystine are provided. The at least two of copper, insulin and cystine may be present in an amount to provide a concentration of the components at provided in Table 1. The kit may contain dried constituents to be reconstituted, and may also contain instructions for use (e.g., for use in supplementing a medium with the kit constituents). The kit may contain the constituents provided herein in amounts suitable to supplement a cell culture medium for use in culturing a mammalian cell comprising a nucleic acid encoding bevacizumab or fragment thereof. In one aspect, a kit comprises cystine in an amount to provide from about 0.9 mM to about 1.5 mM cystine in the cell culture medium. In some embodiments herein, the kit further comprises insulin in an amount to provide from about 1.4 mg/L to about 11 mg/L insulin in the cell culture medium. In some embodiments herein, the kit further comprises copper in an amount to provide from about 26 nM to about 400 nM copper in the cell culture medium. In some embodiments, a kit comprises two or more constituents selected from the group consisting of insulin in an amount to provide from about 7.0 mg/L to about 11.0 mg/L insulin in the cell culture medium, cystine in an amount to provide from about 0.8 mM to about 2.5 mM cystine in the cell culture medium, and copper in an amount to provide from about 25.0 nM to about 400.0 nM copper in the cell culture medium.

In any of the aspects herein, the kit may further comprise an animal-derived hydrolysate or a plant-derived hydrolysate or both an animal-derived hydrolysate and a plant-derived hydrolysate. In some of the embodiments herein, the kit further comprises a plant-derived hydrolysate in an amount to provide from about 1.4 g/L to about 6.2 g/L plant-derived hydrolysate in the cell culture medium. In some of the embodiments herein, the kit further comprises an animal-derived hydrolysate in an amount to provide from about 5.6 g/L to about 38.0 g/L animal-derived hydrolysate in the cell culture medium.

In another aspect of the invention, an article of manufacture is provided comprising a container which holds the cell culture medium of the invention and optionally provides instructions for its use. Suitable containers include, for example, bottles and bags. The container may be formed from a variety of materials such as glass or plastic. The container holds the cell culture medium and the label on, or associated with, the container may indicate directions for use (e.g., for use in culturing cells). The article of manufacture may further include other materials desirable from a commercial and user standpoint, including other buffers, diluents and package inserts with instructions for use.

An article of manufacture comprising a container which holds bevacizumab, or a fragment thereof produced by a method detailed herein and optionally provides instructions for its use is also provided.

EMBODIMENTS

Various embodiments and aspects of the invention are detailed herein and throughout. Embodiments include, without limitation, the following:

Method 1: A method of producing bevacizumab, or a fragment thereof, comprising the step of culturing a mammalian cell comprising a nucleic acid encoding bevacizumab or fragment thereof in a cell culture medium, wherein the cell culture medium comprises two or more components selected from the group consisting of copper, insulin, and cystine, and wherein the cell produces bevacizumab, or a fragment thereof.

Method 2: A method of culturing a mammalian cell comprising a nucleic acid encoding bevacizumab, or a fragment thereof, the method comprising the step of contacting the mammalian cell with a cell culture medium comprising two or more components selected from the group consisting of copper, insulin and cystine.

Method 3: A method of enhancing the amount of bevacizumab, or a fragment thereof, produced from a mammalian cell comprising a nucleic acid encoding bevacizumab, or a fragment thereof, the method comprising the step of culturing the mammalian cell in a cell culture medium comprising at least two of insulin, copper and cystine, wherein the amount of bevacizumab, or a fragment thereof, produced from the mammalian cell is enhanced relative to culturing the mammalian cell in a cell culture medium without at least two of insulin, copper and cystine.

Method 4: A method of culturing a mammalian cell comprising a nucleic acid encoding bevacizumab, or a fragment thereof, in a cell culture medium comprising at least two of insulin, copper and cystine, wherein the amount of bevacizumab, or a fragment thereof, produced from the mammalian cell is enhanced relative to culturing the mammalian cell in a cell culture medium without at least two of insulin, copper and cystine.

For any of methods 1-4, the method may comprise any one or more of the following features (i)-(xviii) or subfeature thereof or any combination of feature or sub feature:
(i) the cell culture medium comprises copper and insulin
(ii) the cell culture medium comprises copper and cystine
(iii) the cell culture medium comprises insulin and cystine
(iv) the cell culture medium comprises copper, insulin, and cystine
(v) the cell culture medium (including a medium containing any of features (i)-(iv)) further comprises a plant-derived hydrolysate, an animal-derived hydrolysate or both a plant-derived hydrolysate and an animal-derived hydrolysate.
(vi) the cell culture medium (including a medium containing any one or more or all of features (i)-(v)) comprises insulin at a concentration of any one of:
  a. from about 1.0 mg/L to about 100.0 mg/L
  b. from about 10.0 mg/L to about 100.0 mg/L
  c. from about 10.0 mg/L to about 50.0 mg/L
  d. from about 10.0 mg/L to about 35.0 mg/L
  e. from about 10.0 mg/L to about 25.0 mg/L
  f. from about 5.0 mg/L to about 80.0 mg/L
  g. from about 5.0 mg/L to about 60.0 mg/L
  h. from about 5.0 mg/L to about 50.0 mg/L
  i. from about 5.0 mg/L to about 40.0 mg/L
  j. from about 5.0 mg/L to about 25.0 mg/L
  k. from about 10.0 mg/L to about 25.0 mg/L
  l. from about 10.0 mg/L to about 40.0 mg/L
  m. from about 15.0 mg/L to about 20.0 mg/L
  n. from about 5.0 mg/L to about 15.0 mg/L
  o. from about 6.0 mg/L to about 12.0 mg/L
  p. from about 7.0 mg/L to about 11.0 mg/L
  q. from about 8.0 mg/L to about 10.0 mg/L
  r. about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L or 31.0 mg/L or 32 mg/L or 33 mg/L or 34 mg/L or 35 mg/L or 36 mg/L or 37 mg/L or 38 mg/L or 39 mg/L or 40 mg/L
  s. about any one of 7 mg/L, 8.0 mg/L, 9.0 mg/L, 10.0 mg/L or 11.0 mg/L
  t. about 25 mg/L
(vii) the cell culture medium (including a medium containing any one or more or all of features (i)-(vi)) comprises copper at a concentration of any one of:
  a. from about 69 nM to about 1,000 nM
  b. from about 69.0 nM to about 400.0 nM
  c. from about 80 nM to about 400 nM.
  d. from about 100 nM to about 400 nM
  e. from about 125 nM to about 400 nM
  f. from about 150 nM to about 400 nM
  g. from about 200 nM to about 400 nM
  h. from about 250 nM to about 400 nM
  i. from about 300 nM to about 400 nM
  j. from about 325 nM to about 375 nM
  k. from about 325 nM to about 350 nM
  l. about any one of 100 nM, 125 nM, 150 nM, 175 nM, 200 nM, 225 nM, 250 nM, 275 nM, 300 nM, 325 nM, 350 nM, 375 nM or 400 nM.
  m. about any one of 330 nM, 335 nM, 340 nM, 345 nM or 350 nM
  n. about 335 nM, 336 nM, 337 nM, 338 nM, 339 nM or 400 nM
  o. about 339 nM
(viii) the cell culture medium (including a medium containing any one or more or all of features (i)-(vii)) comprises cystine at a concentration of any one of:
  a. from about 0.7 mM to about 2.0 mM
  b. from about 0.8 mM to about 2.5 mM
  c. from about 0.8 mM to about 2.0 mM
  d. from about 0.8 mM to about 1.75 mM
  e. from about 0.8 mM to about 1.6 mM
  f. from about 1.0 mM to about 2.0 mM
  g. from about 1.0 mM to about 1.6 mM
  h. from about 1.2 mM to about 1.4 mM
  i. about any one of 0.8 mM or 0.9 mM or 1.0 mM or 1.1 mM or 1.2 mM or 1.3 mM or 1.4 mM or 1.5 mM
  j. about any one of 1.1 mM, 1.3 mM or 1.5 mM
(ix) the cell culture medium (including a medium containing any one or more or all of features (i)-(viii)) comprises an animal-derived hydrolysate at a concentration of any one of:
  a. from about 6.0 g/L to about 20.0 g/L
  b. from about 5.6 g/L to about 38.0 g/L
  c. from about 7.0 g/L to about 25.0 g/L
  d. from about 7.0 g/L to about 20.0 g/L
  e. from about 7.0 g/L to about 15.0 g/L
  f. from about 8.0 g/L to about 12.0 g/L
  g. from about 9.0 g/L to about 11.0 g/L
  h. from about 7.0 g/L to about 11.0 g/L
  i. about any one of 5 g/L, 10 g/L, 15 g/L, 20 g/L, 25 g/L, 30 g/L, 35 g/L, 40 g/L, 45 g/L or 50 g/L
  j. about any one of 5 g/L, 6 g/L, 7 g/L, 8 g/L, 9 g/L, 10 g/L, 11 g/L, or 12 g/L
  k. about 10 g/L
  l. about 13 g/L
(x) the cell culture medium (including a medium containing any one or more or all of features (i)-(ix)) comprises a plant-derived hydrolysate at a concentration of any one of:
  a. from about 1.0 g/L to about 10.0 g/L
  b. from about 1.4 g/L to about 11.0 g/L
  c. from about 1.4 g/L to about 6.2 g/L
  d. from about 1.5 g/L to about 5.5 g/L
  e. from about 1.5 g/L to about 4.5 g/L
  f. from about 1.5 g/L to about 3.5 g/L
  g. from about 2.0 g/L to about 3.0 g/L
  h. from about 1.5 g/L to about 2.5 g/L
  i. from about 1.75 g/L to about 2.75 g/L
  j. from about 2.25 g/L to about 2.75 g/L
  k. about any one of 1.75 g/L, 2.0 g/L, 2.25 g/L, 2.5 g/L, 3.0 g/L, 3.25, 3.5 g/L, 3.75 g/L, or 4.0 g/L
  l. about any one of 2.0 g/L, 2.25 g/L, 2.5 g/L or 3.0 g/L m. about 2.5 g/L
n. about 3.1 g/L
(xi) the cell culture medium (including a medium containing any one or more or all of features (i)-(x)) comprises both an animal-derived hydrolysate and a plant-derived hydrolysate, and wherein the animal-derived hydrolysate is present in a greater amount than the plant-derived hydrolysate
(xii) the cell culture medium (including a medium containing any one or more or all of features (i)-(xi)) comprises insulin and the method further comprises the step of adding an additional amount of insulin to the cell culture medium, wherein the additional amount of insulin may: (a) be added to the cell culture medium once or at least three times or at least six times during the cell culture cycle and (b) may be added in an amount to provide insulin in the cell culture medium at a concentration of any one of:
  a. from about 1.0 mg/L to about 100.0 mg/L
  b. from about 10.0 mg/L to about 100.0 mg/L
  c. from about 10.0 mg/L to about 50.0 mg/L
  d. from about 10.0 mg/L to about 35.0 mg/L
  e. from about 10.0 mg/L to about 25.0 mg/L
  f. from about 5.0 mg/L to about 80.0 mg/L
  g. from about 5.0 mg/L to about 60.0 mg/L
  h. from about 5.0 mg/L to about 50.0 mg/L
  i. from about 5.0 mg/L to about 40.0 mg/L
  j. from about 5.0 mg/L to about 25.0 mg/L
  k. from about 10.0 mg/L to about 25.0 mg/L
  l. from about 10.0 mg/L to about 40.0 mg/L
  m. from about 15.0 mg/L to about 20.0 mg/L
  n. from about 5.0 mg/L to about 15.0 mg/L
  o. from about 6.0 mg/L to about 12.0 mg/L
  p. from about 7.0 mg/L to about 11.0 mg/L
  q. from about 8.0 mg/L to about 10.0 mg/L
  r. about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L or 31.0 mg/L or 32 mg/L or 33 mg/L or 34 mg/L or 35 mg/L or 36 mg/L or 37 mg/L or 38 mg/L or 39 mg/L or 40 mg/L
  s. about any one of 7 mg/L, 8.0 mg/L, 9.0 mg/L, 10.0 mg/L or 11.0 mg/L
  t. about 25 mg/L
  u. about 15 mg/L
(xiii) the method further comprises the step of adding cysteine to the cell culture medium (including a medium containing any one or more or all of features (i)-(xii)), which cysteine may be added to the cell culture medium (a) as a component of a batch feed that is added to a basal medium that does not comprise cysteine and/or (b) may be added in an amount to provide cysteine in the cell culture medium at a concentration of from about 0.5 to about 5.0 mM or from about 0.5 to about 2.0 mM or from about 0.5 to about 2.0 mM (such as at a concentration of 0.8 mM) or from about 7.0 to about 8.0 mM (such as at a concentration of about 7.5 mM)
(xiv) the method further comprises the step of adding cystine to the cell culture medium (including a medium containing any one or more or all of features (i)-(xii)), which cystine may be added to the cell culture medium as a component of a batch feed that is added to a basal medium and which may be added in an amount to provide cystine in the cell culture medium at a concentration of from about 0.1 to about 1.5 mM (such as at a concentration of 0.2 mM)
(xv) the cell is cultured (e.g., in any cell culture media including those having any one or more or all of features (i)-(xiv)) at a temperature ranging from about 28° C. to about 37° C. or from about 31° C. to about 35° C.
(xvi) the cell is cultured (e.g., in any cell culture media including those having any one or more or all of features (i)-(xiv)) at a first temperature of about 35° C. for a first period of time, is cultured at a second temperature of about 33° C. for a second period of time, and is cultured at a third temperature of about 31° C. for a third period of time
(xvii) bevacizumab, or a fragment thereof, is secreted into the cell culture medium (including a medium containing any one or more or all of features (i)-(xvi))
(xviii) the method further comprises the step of recovering the bevacizumab, or a fragment thereof, from the cell culture (including a medium containing any one or more or all of features (i)-(xvi))

Also provided herein is bevacizumab, or fragment thereof, produced by any method provided herein, including without limitation any of methods 1-4, which method may further comprise any one or more or all of the features (i)-(xviii) or sub-feature thereof or any combination of the foregoing.

Also provided is a composition comprising: (i) bevacizumab, or a fragment thereof, produced by any method provided herein, including without limitation any of methods 1-4, which method may further comprise any one or more or all of the features (i)-(xviii) or sub-feature thereof or any combination of the foregoing and (ii) a pharmaceutically acceptable carrier.

A kit for supplementing a cell culture medium for use in culturing a mammalian cell comprising a nucleic acid encoding bevacizumab, or a fragment thereof, is also provided, the kit comprising at least two of components (i)-(iii):
(i) insulin in an amount to provide a concentration of any one of:
  a. from about 1.0 mg/L to about 100.0 mg/L
  b. from about 10.0 mg/L to about 100.0 mg/L
  c. from about 10.0 mg/L to about 50.0 mg/L
  d. from about 10.0 mg/L to about 35.0 mg/L
  e. from about 10.0 mg/L to about 25.0 mg/L
  f. from about 5.0 mg/L to about 80.0 mg/L
  g. from about 5.0 mg/L to about 60.0 mg/L
  h. from about 5.0 mg/L to about 50.0 mg/L
  i. from about 5.0 mg/L to about 40.0 mg/L
  j. from about 5.0 mg/L to about 25.0 mg/L
  k. from about 10.0 mg/L to about 25.0 mg/L
  l. from about 10.0 mg/L to about 40.0 mg/L
  m. from about 15.0 mg/L to about 20.0 mg/L
  n. from about 5.0 mg/L to about 15.0 mg/L
  o. from about 6.0 mg/L to about 12.0 mg/L
  p. from about 7.0 mg/L to about 11.0 mg/L
  q. from about 8.0 mg/L to about 10.0 mg/L
  r. about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L or 31.0 mg/L or 32 mg/L or 33 mg/L or 34 mg/L or 35 mg/L or 36 mg/L or 37 mg/L or 38 mg/L or 39 mg/L or 40 mg/L s. about any one of 7 mg/L, 8.0 mg/L, 9.0 mg/L, 10.0 mg/L or 11.0 mg/L.
t. about 25 mg/L (ii) cystine in an amount to provide a concentration of any one of:
  a. from about 0.7 mM to about 2.0 mM
  b. from about 0.8 mM to about 2.5 mM
  c. from about 0.8 mM to about 2.0 mM
  d. from about 0.8 mM to about 1.75 mM
  e. from about 0.8 mM to about 1.6 mM
  f. from about 1.0 mM to about 2.0 mM
  g. from about 1.0 mM to about 1.6 mM
  h. from about 1.2 mM to about 1.4 mM
  i. about any one of 0.8 mM or 0.9 mM or 1.0 mM or 1.1 mM or 1.2 mM or 1.3 mM or 1.4 mM or 1.5 mM
  j. about any one of 1.1 mM, 1.3 mM or 1.5 mM (iii) copper at a concentration of any one of:
  a. from about 69.0 nM to about 1,000.0 nM
  b. from about 69.0 nM to about 400.0 nM
  c. from about 80 nM to about 400 nM.
  d. from about 100 nM to about 400 nM
  e. from about 125 nM to about 400 nM
  f. from about 150 nM to about 400 nM
  g. from about 200 nM to about 400 nM
  h. from about 250 nM to about 400 nM
  i. from about 300 nM to about 400 nM
  j. from about 325 nM to about 375 nM
  k. from about 325 nM to about 350 nM
  l. about any one of 100 nM, 125 nM, 150 nM, 175 nM, 200 nM, 225 nM, 250 nM, 275 nM, 300 nM, 325 nM, 350 nM, 375 nM or 400 nM.
  m. about any one of 330 nM, 335 nM, 340 nM, 345 nM or 350 nM
  n. about 335 nM, 336 nM, 337 nM, 338 nM, 339 nM or 400 nM
  o. about 339 nM The kit may further comprise other components, including any one or more of:
  i. an animal-derived hydrolysate, such as in an amount to provide concentration of any one of:
    a. from about 6.0 g/L to about 20.0 g/L
    b. from about 5.6 g/L to about 38.0 g/L
    c. from about 7.0 g/L to about 25.0 g/L
    d. from about 7.0 g/L to about 20.0 g/L
    e. from about 7.0 g/L to about 15.0 g/L
    f. from about 8.0 g/L to about 12.0 g/L
    g. from about 9.0 g/L to about 11.0 g/L
    h. from about 7.0 g/L to about 11.0 g/L
    i. about any one of 5 g/L, 10 g/L, 15 g/L, 20 g/L, 25 g/L, 30 g/L, 35 g/L, 40 g/L, 45 g/L or 50 g/L
    j. about any one of 5 g/L, 6 g/L, 7 g/L, 8 g/L, 9 g/L, 10 g/L, 11 g/L, or 12 g/L
    k. about 10 g/L
    l. about 13 g/L
  ii. plant-derived hydrolysate, such as in an amount to provide a concentration of any one of:
    a. from about 1.0 g/L to about 10.0 g/L
    b. from about 1.4 g/L to about 11.0 g/L
    c. from about 1.4 g/L to about 6.2 g/L
    d. from about 1.5 g/L to about 5.5 g/L
    e. from about 1.5 g/L to about 4.5 g/L
    f. from about 1.5 g/L to about 3.5 g/L
    g. from about 2.0 g/L to about 3.0 g/L
    h. from about 1.5 g/L to about 2.5 g/L
    i. from about 1.75 g/L to about 2.75 g/L
    j. from about 2.25 g/L to about 2.75 g/L
    k. about any one of 1.75 g/L, 2.0 g/L, 2.25 g/L, 2.5 g/L, 3.0 g/L, 3.25, 3.5 g/L, 3.75 g/L, or 4.0 g/L
    l. about any one of 2.0 g/L, 2.25 g/L, 2.5 g/L or 3.0 g/L
    m. about 2.5 g/L
    n. about 3.1 g/L A cell culture medium for use in culturing a mammalian cell comprising a nucleic acid encoding bevacizumab, or a fragment thereof, is also provided, the cell culture medium comprising at least two of components (i)-(iii):

(i) insulin in an amount to provide a concentration of any one of:
  a. from about 1.0 mg/L to about 100.0 mg/L
  b. from about 10.0 mg/L to about 100.0 mg/L
  c. from about 10.0 mg/L to about 50.0 mg/L
  d. from about 10.0 mg/L to about 35.0 mg/L
  e. from about 10.0 mg/L to about 25.0 mg/L
  f. from about 5.0 mg/L to about 80.0 mg/L
  g. from about 5.0 mg/L to about 60.0 mg/L
  h. from about 5.0 mg/L to about 50.0 mg/L
  i. from about 5.0 mg/L to about 40.0 mg/L
  j. from about 5.0 mg/L to about 25.0 mg/L
  k. from about 10.0 mg/L to about 25.0 mg/L
  l. from about 10.0 mg/L to about 40.0 mg/L
  m. from about 15.0 mg/L to about 20.0 mg/L
  n. from about 5.0 mg/L to about 15.0 mg/L
  o. from about 6.0 mg/L to about 12.0 mg/L
  p. from about 7.0 mg/L to about 11.0 mg/L
  q. from about 8.0 mg/L to about 10.0 mg/L
  r. about any one of 5.0 mg/L, 6.0 mg/L, 7.0 mg/L, 8.0 mg/L, 9.0 mg/L, 10.0 mg/L, 11.0 mg/L, 12.0 mg/L, 13.0 mg/L, 14.0 mg/L, 15.0 mg/L, 16.0 mg/L, 17.0 mg/L, 18.0 mg/L, 19.0 mg/L, 20.0 mg/L, 21.0 mg/L, 22.0 mg/L, 23.0 mg/L, 24.0 mg/L, 25.0 mg/L, 26.0 mg/L, 27.0 mg/L, 28.0 mg/L, 29.0 mg/L or 30.0 mg/L or 31.0 mg/L or 32 mg/L or 33 mg/L or 34 mg/L or 35 mg/L or 36 mg/L or 37 mg/L or 38 mg/L or 39 mg/L or 40 mg/L
  s. about any one of 7 mg/L, 8.0 mg/L, 9.0 mg/L, 10.0 mg/L or 11.0 mg/L
  t. about 25 mg/L (ii) cystine in an amount to provide a concentration of any one of:
  a. from about 0.7 mM to about 2.0 mM
  b. from about 0.8 mM to about 2.5 mM
  c. from about 0.8 mM to about 2.0 mM
  d. from about 0.8 mM to about 1.75 mM
  e. from about 0.8 mM to about 1.6 mM
  f. from about 1.0 mM to about 2.0 mM
  g. from about 1.0 mM to about 1.6 mM
  h. from about 1.2 mM to about 1.4 mM
  i. about any one of 0.8 mM or 0.9 mM or 1.0 mM or 1.1 mM or 1.2 mM or 1.3 mM or 1.4 mM or 1.5 mM
  j. about any one of 1.1 mM, 1.3 mM or 1.5 mM (iii) copper at a concentration of any one of:
  a. from about 69.0 nM to about 1,000.0 nM
  b. from about 69.0 nM to about 400.0 nM
  c. from about 80 nM to about 400 nM.
  d. from about 100 nM to about 400 nM
  e. from about 125 nM to about 400 nM
  f. from about 150 nM to about 400 nM
  g. from about 200 nM to about 400 nM
  h. from about 250 nM to about 400 nM
  i. from about 300 nM to about 400 nM
  j. from about 325 nM to about 375 nM
  k. from about 325 nM to about 350 nM l. about any one of 100 nM, 125 nM, 150 nM, 175 nM, 200 nM, 225 nM, 250 nM, 275 nM, 300 nM, 325 nM, 350 nM, 375 nM or 400 nM.
m. about any one of 330 nM, 335 nM, 340 nM, 345 nM or 350 nM
n. about 335 nM, 336 nM, 337 nM, 338 nM, 339 nM or 400 nM
o. about 339 nM The cell culture medium may comprise other components, including any one or more of:
1) an animal-derived hydrolysate, such as in an amount to provide concentration of any one of:
   a. from about 6.0 g/L to about 20.0 g/L
   b. from about 5.6 g/L to about 25.0 g/L
   c. from about 7.0 g/L to about 25.0 g/L
   d. from about 7.0 g/L to about 20.0 g/L
   e. from about 7.0 g/L to about 15.0 g/L
   f. from about 8.0 g/L to about 12.0 g/L
   g. from about 9.0 g/L to about 11.0 g/L
   h. from about 7.0 g/L to about 11.0 g/L
   i. about any one of 5 g/L, 10 g/L, 15 g/L, 20 g/L or 25 g/L
   j. about any one of 5 g/L, 6 g/L, 7 g/L, 8 g/L, 9 g/L, 10 g/L, 11 g/L, or 12 g/L
   k. about 10 g/L
   l. about 13 g/L
2) plant-derived hydrolysate, such as in an amount to provide a concentration of any one of:
   a. from about 1.0 g/L to about 10.0 g/L
   b. from about 1.4 g/L to about 11.0 g/L
   c. from about 1.4 g/L to about 6.2 g/L
   d. from about 1.5 g/L to about 5.5 g/L
   e. from about 1.5 g/L to about 4.5 g/L
   f. from about 1.5 g/L to about 3.5 g/L
   g. from about 2.0 g/L to about 3.0 g/L
   h. from about 1.5 g/L to about 2.5 g/L
   i. from about 1.75 g/L to about 2.75 g/L
   j. from about 2.25 g/L to about 2.75 g/L
   k. about any one of 1.75 g/L, 2.0 g/L, 2.25 g/L, 2.5 g/L, 3.0 g/L, 3.25 g/L, 3.5 g/L, 3.75 g/L, or 4.0 g/L
   l. about any one of 2.0 g/L, 2.25 g/L, 2.5 g/L or 3.0 g/L
   m. about 2.5 g/L
   n. about 3.1 g/L The cell culture medium may further be supplemented with additional cell culture medium components, where the additional cell culture medium components may comprise, e.g., insulin and/or cysteine, such as insulin in an amount to provide any concentration of insulin provided herein, including the concentrations listed in the present embodiments (such as 15 mg/L) and/or cysteine in an amount to provide any concentration of cysteine provided herein (such as 0.8 mM), including the concentrations listed in the present embodiments.

The cell culture medium may further be supplemented with additional cell culture medium components, where the additional cell culture medium components may comprise, e.g., insulin and/or cysteine and/or cystine, such as insulin in an amount to provide any concentration of insulin provided herein, including the concentrations listed in the present embodiments (such as 15 mg/L) and/or cysteine in an amount to provide any concentration of cysteine provided herein (such as 0.8 mM), including the concentrations listed in the present embodiments and/or cystine in an amount to provide any concentration of cystine provided herein (such as 0.2 mM), including the concentrations listed in the present embodiments.

Also provided herein is a composition comprising (a) a mammalian cell comprising a nucleic acid encoding bevacizumab, or a fragment thereof; and (b) a cell culture medium detailed herein, including without limitation a cell culture medium provided in the present embodiments. Further provided is a composition comprising: (a) bevacizumab, or a fragment thereof; and (b) a cell culture medium detailed herein, including without limitation a cell culture medium provided in the present embodiments.

The following Examples are provided to illustrate but not to limit the invention.

EXAMPLES

Example 1

Impact of Cell Culture Medium Components on Amount of Bevacizumab Produced by a Mammalian Cell Line Chinese hamster ovary (CHO) cells producing bevacizumab were cultured in cell culture media containing various amounts of insulin, and the impact of insulin on the amount of bevacizumab produced was assessed. Production of bevacizumab was initiated in cell culture by inoculating cells in basal medium containing 339 nM copper, 1% animal hydrolysate and 0.25% plant hydrolysate and a batch feed medium was added on day 3 over a 14 day cell culture cycle in a bioreactor. The basal cell culture medium of a control cell culture was supplemented with less than 10 mg/L of insulin and no additional insulin was given during the cell culture cycle. In two representative experimental cases (case 1 and case 2), the insulin level in the basal cell culture media was 10 mg/L. Additional insulin was added three to six times during the cell culture cycle so as to provide cell culture case 1 and cell culture case 2 with a final amount of 25 mg/L and 40 mg/L insulin at the end of the 14 day cell culture cycle, respectively (Table A). The cells were cultured at 37° C. on day 1 and the temperature was subsequently shifted down to 35° C. on day 1, 33° C. on day 8, and 31° C. on day 10. Titer improvement was quantified by percent increase over the control. Total addition of insulin during the cell culture cycle from less than 10 mg/L to 25 mg/L or 40 mg/L led to a titer improvement of about 16% or about 18% as compared with the control, respectively (Table A).

TABLE A

Exemplary insulin addition protocol and results

| | Insulin addition case 1 | Insulin addition case 2 |
|---|---|---|
| Total insulin concentration added during a 14 day duration | 25 mg/L | 40 mg/L |
| Titer improvement percent increase | 16% | 18% |

CHO cells producing bevacizumab were cultured in cell culture media containing different amounts of hydrolysate from different sources and the impact of the specific hydrolysate on the amount of bevacizumab produced was assessed. In two representative protocols, production of bevacizumab was initiated in cell culture by inoculating cells in basal cell culture medium containing 339 nM copper and a batch feed medium was added on day 3 over a 14 day cell culture cycle in a bioreactor. The basal cell culture medium for Protocol 1 had 1% animal-derived hydrolysate without plant-derived hydrolysate while Protocol 2 had basal cell culture medium supplemented with 0.75% animal-derived hydrolysate in combination with 0.25% plant-derived hydrolysate (Table B). Analysis of the antibody titer produced by the two protocols demonstrated that Protocol 2 provided a 27% increase in the amount of bevacizumab produced from the cells as compared to the amount of bevacizumab produced by cells cultured using Protocol 1 (Table B).

TABLE B

Exemplary experimental protocols

|  | Protocol 1 | Protocol 2 |
| --- | --- | --- |
| Porcine peptone | 1% | 0.75% |
| Plant peptone | None | 0.25% |
| Titer improvement percent increase | Not Applicable | 27% |

Example 2

Impact of Cell Culture Medium Components on Amount of Bevacizumab Produced by a Mammalian Cell Line CHO cells producing bevacizumab were cultured in basal media with either the amino acid cysteine in the monomer form (Cys, cysteine) or in the dimer form (Cys-Cys, cystine) (Table C). Production of bevacizumab was initiated in cell culture by inoculating cells in basal medium containing 339 nM copper, 1% animal hydrolysate and 0.25% plant hydrolysate and a batch feed was added on day 3 over a 14 day cell culture cycle in a bioreactor. Insulin levels in the basal media were at a concentration of either less than 10 mg/L or 10 mg/L. Two of the experimental cell cultures (Cysteine+Insulin and Cystine+Insulin) had additional insulin added three times or six times during the cell culture cycle so as to provide a final amount of 25 mg/L or 40 mg/L (Table C). The cells were cultured at 37° C. on day 1 the temperature was subsequently shifted down to 35° C. on day 1, 33° C. on day 8, and 31° C. on day 10. Titer improvement was quantified by percent increase over the control. Replacement of cysteine (Cys) by cystine (Cys-Cys) improved titer by 11% over the control. Impact of insulin addition was also observed in basal media made using cystine (Cys-Cys).

TABLE C

Summary of protocols and results

|  | Cysteine (Control) | Cystine | Cysteine + Insulin | Cystine + Insulin |
| --- | --- | --- | --- | --- |
| Cysteine (Cys) concentration in basal media | 2.6 mM | 0 mM | 2.6 mM | 0 mM |
| Cystine (Cys-Cys) concentration in basal media | 0 mM | 1.3 mM | 0 mM | 1.3 mM |
| Total insulin concentration added during a 14 day duration | Less than 10 mg/L | Less than 10 mg/L | 25 mg/L | 40 mg/L |

TABLE C-continued

Summary of protocols and results

|  | Cysteine (Control) | Cystine | Cysteine + Insulin | Cystine + Insulin |
| --- | --- | --- | --- | --- |
| Titer improvement percent increase | Not Applicable | 11% | 11% | 14% |

What is claimed is:

1. A method of producing bevacizumab, or a fragment thereof, comprising the step of culturing a Chinese hamster ovary (CHO) cell comprising a nucleic acid encoding bevacizumab or fragment thereof in a cell culture medium, wherein the cell culture medium comprises copper, insulin, and cystine, wherein the cystine is at a concentration of from 1.25 mM to 2.5 mM, and wherein the cell produces bevacizumab, or a fragment thereof.

2. The method of claim 1, wherein the cell culture medium further comprises a plant peptone, a porcine peptone, or both a plant peptone and a porcine peptone.

3. The method of claim 1, wherein the cell culture medium comprises insulin at a concentration of from about 1.0 mg/L to about 100.0 mg/L.

4. The method of claim 1, wherein the cell culture medium comprises insulin at a concentration of from about 10.0 mg/L to about 100.0 mg/L.

5. The method of claim 1, wherein the cell culture medium comprises insulin at a concentration of from about 10.0 mg/L to about 50.0 mg/L.

6. The method of claim 1, wherein the cell culture medium comprises insulin at a concentration of from about 10.0 mg/L to about 35.0 mg/L.

7. The method of claim 1, wherein the cell culture medium comprises insulin at a concentration of from about 10.0 mg/L to about 25.0 mg/L.

8. The method of claim 1, wherein the cell culture medium comprises insulin at a concentration of about 25 mg/L.

9. The method of claim 1, wherein the cell culture medium comprises copper at a concentration of from about 69 nM to about 1,000 nM.

10. The method of claim 1, wherein the cell culture medium comprises copper at a concentration of from about 325 nM to about 375 nM.

11. The method of claim 1, wherein the cell culture medium comprises copper at a concentration of from about 325 nM to about 350 nM.

12. The method of claim 1, wherein the cell culture medium comprises copper at a concentration of about any one of 330 nM, 335 nM, 339 nM, 340 nM, 345 nM or 350 nM.

13. The method of claim 1, wherein the cell culture medium comprises copper at a concentration of about 339 nM.

14. The method of claim 1, wherein the cell culture medium comprises cystine at a concentration of about 1.3 mM.

15. The method of claim 1, wherein the cell culture medium comprises a porcine peptone at a concentration of from about 6.0 g/L to about 20.0 g/L.

16. The method of claim 1, wherein the cell culture medium comprises a porcine peptone at a concentration of from about 8.0 g/L to about 12.0 g/L.

17. The method of claim 1, wherein the cell culture medium comprises a porcine peptone at a concentration of from about 9.0 g/L to about 11.0 g/L.

18. The method of claim 1, wherein the cell culture medium comprises a porcine peptone at a concentration of about 13 g/L.

19. The method of claim 1, wherein the cell culture medium comprises a plant peptone at a concentration of from about 1.0 g/L to about 10.0 g/L.

20. The method of claim 1, wherein the cell culture medium comprises a plant peptone at a concentration of from about 2.0 g/L to about 3.0 g/L.

21. The method of claim 1, wherein the cell culture medium comprises a plant peptone at a concentration of from about 2.25 g/L to about 2.75 g/L.

22. The method of claim 1, wherein the cell culture medium comprises a plant peptone at a concentration of about 3.1 g/L.

23. The method of claim 1, wherein the cell culture medium comprises insulin and the method further comprises the step of adding an additional amount of insulin to the cell culture medium.

24. The method of claim 23, wherein the additional amount of insulin is added to the cell culture medium once during the cell culture cycle.

25. The method of claim 23, wherein the additional amount of insulin is added to the cell culture medium at least three times during the cell culture cycle.

26. The method of claim 23, wherein the additional amount of insulin is added to the cell culture medium at least six times during the cell culture cycle.

27. The method of claim 23, wherein the additional amount of insulin is added in an amount to provide insulin in the cell culture medium at a concentration of from about 1.0 mg/L to about 100.0 mg/L.

28. The method of claim 23, wherein the additional amount of insulin is added in an amount to provide insulin in the cell culture medium at a concentration of from about 10.0 mg/L to about 100.0 mg/L.

29. The method of claim 23, wherein the additional amount of insulin is added in an amount to provide insulin in the cell culture medium at a concentration of from about 10.0 mg/L to about 50.0 mg/L.

30. The method of claim 23, wherein the additional amount of insulin is added in an amount to provide insulin in the cell culture medium at a concentration of from about 10.0 mg/L to about 35.0 mg/L.

31. The method of claim 23, wherein the additional amount of insulin is added in an amount to provide insulin in the cell culture medium at a concentration of from about 10.0 mg/L to about 25.0 mg/L.

32. The method of claim 23, wherein the additional amount of insulin is added in an amount to provide insulin in the cell culture medium at a concentration of about 15 mg/L.

33. The method of claim 1, wherein the method further comprises the step of adding cysteine to the cell culture medium.

34. The method of claim 33, wherein cysteine is added in an amount to provide from about 0.5 to about 2.0 mM cysteine in the cell culture medium.

35. The method of claim 33, wherein cysteine is added in an amount to provide about 0.8 mM cysteine in the cell culture medium.

36. The method of claim 1, wherein the cell is cultured at a temperature ranging from about 28° C. to about 37° C.

37. The method of claim 36, wherein the cell is cultured at a temperature ranging from about 31° C. to about 35° C.

38. The method of claim 1, wherein the cell is cultured at a first temperature of about 35° C. for a first period of time, is cultured at a second temperature of about 33° C. for a second period of time, and is cultured at a third temperature of about 31° C. for a third period of time.

39. The method of claim 1, wherein bevacizumab, or a fragment thereof, is secreted into the cell culture medium.

40. The method of claim 1, further comprising the step of recovering the bevacizumab, or a fragment thereof, from the cell culture.

41. A method of culturing a Chinese hamster ovary (CHO) cell comprising a nucleic acid encoding bevacizumab, or a fragment thereof, the method comprising the step of contacting the CHO cell with a cell culture medium comprising copper, insulin and cystine, wherein the cystine is at a concentration of from 1.25 mM to 2.5 mM.

42. The method of claim 41, wherein the cell culture medium further comprises a a plant peptone, a porcine peptone, or both a plant peptone and a porcine peptone.

43. The method of claim 41, wherein the cell culture medium comprises insulin at a concentration of from about 1.0 mg/L to about 100.0 mg/L.

44. The method of claim 41, wherein the cell culture medium comprises insulin at a concentration of from about 10.0 mg/L to about 100.0 mg/L.

45. The method of claim 41, wherein the cell culture medium comprises insulin at a concentration of from about 10.0 mg/L to about 50.0 mg/L.

46. The method of claim 41, wherein the cell culture medium comprises insulin at a concentration of from about 10.0 mg/L to about 35.0 mg/L.

47. The method of claim 41, wherein the cell culture medium comprises insulin at a concentration of from about 10.0 mg/L to about 25.0 mg/L.

48. The method of claim 41, wherein the cell culture medium comprises insulin at a concentration of about 25 mg/L.

49. The method of claim 41, wherein the cell culture medium comprises copper at a concentration of from about 69 nM to about 1,000 nM.

50. The method of claim 41, wherein the cell culture medium comprises copper at a concentration of from about 325 nM to about 375 nM.

51. The method of claim 41, wherein the cell culture medium comprises copper at a concentration of from about 325 nM to about 350 nM.

52. The method of claim 41, wherein the cell culture medium comprises copper at a concentration of about any one of 330 nM, 335 nM, 339 nM, 340 nM, 345 nM or 350 nM.

53. The method of claim 41, wherein the cell culture medium comprises copper at a concentration of about 339 nM.

54. The method of claim 41, wherein the cell culture medium comprises cystine at a concentration of about 1.3 mM.

55. The method of claim 41, wherein the cell culture medium comprises a porcine peptone at a concentration of from about 6.0 g/L to about 20.0 g/L.

56. The method of claim 41, wherein the cell culture medium comprises a porcine peptone at a concentration of from about 8.0 g/L to about 12.0 g/L.

57. The method of claim 41, wherein the cell culture medium comprises a porcine peptone at a concentration of from about 9.0 g/L to about 11.0 g/L.

58. The method of claim 41, wherein the cell culture medium comprises a porcine peptone at a concentration of about 13 g/L.

59. The method of claim 41, wherein the cell culture medium comprises a plant peptone at a concentration of from about 1.0 g/L to about 10.0 g/L.

60. The method of claim 41, wherein the cell culture medium comprises a plant peptone at a concentration of from about 2.0 g/L to about 3.0 g/L.

61. The method of claim 41, wherein the cell culture medium comprises a plant peptone at a concentration of from about 2.25 g/L to about 2.75 g/L.

62. The method of claim 41, wherein the cell culture medium comprises a plant peptone at a concentration of about 3.1 g/L.

63. The method of claim 41, wherein the cell culture medium comprises insulin and the method further comprises the step of adding an additional amount of insulin to the cell culture medium.

64. The method of claim 63, wherein the additional amount of insulin is added to the cell culture medium once during the cell culture cycle.

65. The method of claim 63, wherein the additional amount of insulin is added to the cell culture medium at least three times during the cell culture cycle.

66. The method of claim 63, wherein the additional amount of insulin is added to the cell culture medium at least six times during the cell culture cycle.

67. The method of claim 63, wherein the additional amount of insulin is added in an amount to provide insulin in the cell culture medium at a concentration of from about 1.0 mg/L to about 100.0 mg/L.

68. The method of claim 63, wherein the additional amount of insulin is added in an amount to provide insulin in the cell culture medium at a concentration of from about 10.0 mg/L to about 100.0 mg/L.

69. The method of claim 63, wherein the additional amount of insulin is added in an amount to provide insulin in the cell culture medium at a concentration of from about 10.0 mg/L to about 50.0 mg/L.

70. The method of claim 63, wherein the additional amount of insulin is added in an amount to provide insulin in the cell culture medium at a concentration of from about 10.0 mg/L to about 35.0 mg/L.

71. The method of claim 63, wherein the additional amount of insulin is added in an amount to provide insulin in the cell culture medium at a concentration of from about 10.0 mg/L to about 25.0 mg/L.

72. The method of claim 63, wherein the additional amount of insulin is added in an amount to provide insulin in the cell culture medium at a concentration of about 15 mg/L.

73. The method of claim 41, wherein the method further comprises the step of adding cysteine to the cell culture medium.

74. The method of claim 73, wherein cysteine is added in an amount to provide from about 0.5 to about 2.0 mM cysteine in the cell culture medium.

75. The method of claim 73, wherein cysteine is added in an amount to provide about 0.8 mM cysteine in the cell culture medium.

76. The method of claim 41, wherein the cell is cultured at a temperature ranging from about 28° C. to about 37° C.

77. The method of claim 76, wherein the cell is cultured at a temperature ranging from about 28° C. to about 35° C.

78. The method of claim 41, wherein the cell is cultured at a first temperature of about 35° C. for a first period of time, is cultured at a second temperature of about 33° C. for a second period of time, and is cultured at a third temperature of about 31° C. for a third period of time.

79. The method of claim 41, wherein bevacizumab, or a fragment thereof, is secreted into the cell culture medium.

80. The method of claim 41, wherein the CHO cell is contacted with the cell culture medium during the cell's growth phase.

81. The method of claim 41, wherein the CHO cell is contacted with the cell culture medium during the cell's production phase.

82. A method of enhancing the amount of bevacizumab, or a fragment thereof, produced from a Chinese hamster ovary (CHO) cell comprising a nucleic acid encoding bevacizumab, or a fragment thereof, the method comprising the step of culturing the CHO cell in a cell culture medium comprising insulin, copper and cystine, wherein the cystine is at a concentration of from 1.25 mM to 2.5 mM, and wherein the amount of bevacizumab, or a fragment thereof, produced from the CHO cell is enhanced relative to culturing the CHO cell in a cell culture medium without insulin, copper and cystine.

83. A method of culturing a Chinese hamster ovary (CHO) cell comprising a nucleic acid encoding bevacizumab, or a fragment thereof, in a cell culture medium comprising insulin, copper and cystine, wherein the cystine is at a concentration of from 1.25 mM to 2.5 mM, and wherein the amount of bevacizumab, or a fragment thereof, produced from the CHO cell is enhanced relative to culturing the CHO cell in a cell culture medium without at least two of insulin, copper and cystine.

84. The method of claim 1, wherein the amount of bevacizumab, or a fragment thereof, produced from the cell is enhanced relative to culturing the cell in a cell culture medium without insulin, copper and cystine.

* * * * *

UNITED STATES PATENT AND TRADEMARK OFFICE
CERTIFICATE OF CORRECTION

| | | |
|---|---|---|
| PATENT NO. | : 9,441,035 B2 | |
| APPLICATION NO. | : 14/211467 | |
| DATED | : September 13, 2016 | |
| INVENTOR(S) | : Carvalhal et al. | |

It is certified that error appears in the above-identified patent and that said Letters Patent is hereby corrected as shown below:

In the Claims

Column 48, Line 20, Claim 42, replace "a a" with --a--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*